(12) United States Patent
Konzny

(10) Patent No.: US 11,986,508 B1
(45) Date of Patent: May 21, 2024

(54) NUTRITIONAL AND COSMETIC PRODUCT, SYSTEM AND METHOD FOR USE

(76) Inventor: Juliana Konzny, Fort Lauderdale, FL (US)

( * ) Notice: Subject to any disclaimer, the term of this patent is extended or adjusted under 35 U.S.C. 154(b) by 945 days.

(21) Appl. No.: 13/537,778

(22) Filed: Jun. 29, 2012

Related U.S. Application Data

(63) Continuation-in-part of application No. 13/080,909, filed on Apr. 6, 2011, now abandoned.

(60) Provisional application No. 61/341,872, filed on Apr. 6, 2010.

(51) Int. Cl.

| | | |
|---|---|---|
| *A61K 36/899* | (2006.01) | |
| *A61K 31/197* | (2006.01) | |
| *A61K 31/355* | (2006.01) | |
| *A61K 31/375* | (2006.01) | |
| *A61K 31/407* | (2006.01) | |
| *A61K 31/4415* | (2006.01) | |
| *A61K 31/59* | (2006.01) | |
| *A61K 31/685* | (2006.01) | |
| *A61K 33/00* | (2006.01) | |
| *A61K 33/06* | (2006.01) | |
| *A61K 36/11* | (2006.01) | |
| *A61K 36/185* | (2006.01) | |
| *A61K 36/23* | (2006.01) | |
| *A61K 36/31* | (2006.01) | |
| *A61K 36/42* | (2006.01) | |
| *A61K 36/55* | (2006.01) | |
| *A61K 36/63* | (2006.01) | |
| *A61K 36/73* | (2006.01) | |
| *A61K 36/736* | (2006.01) | |
| *A61K 36/752* | (2006.01) | |
| *A61K 36/87* | (2006.01) | |
| *A61K 36/886* | (2006.01) | |
| *A61K 36/889* | (2006.01) | |
| *A61K 36/898* | (2006.01) | |

(52) U.S. Cl.
CPC .......... *A61K 36/899* (2013.01); *A61K 31/197* (2013.01); *A61K 31/355* (2013.01); *A61K 31/375* (2013.01); *A61K 31/407* (2013.01); *A61K 31/4415* (2013.01); *A61K 31/59* (2013.01); *A61K 31/685* (2013.01); *A61K 33/00* (2013.01); *A61K 33/06* (2013.01); *A61K 36/11* (2013.01); *A61K 36/185* (2013.01); *A61K 36/23* (2013.01); *A61K 36/31* (2013.01); *A61K 36/42* (2013.01); *A61K 36/55* (2013.01); *A61K 36/63* (2013.01); *A61K 36/73* (2013.01); *A61K 36/736* (2013.01); *A61K 36/752* (2013.01); *A61K 36/87* (2013.01); *A61K 36/886* (2013.01); *A61K 36/889* (2013.01); *A61K 36/898* (2013.01)

(58) Field of Classification Search
None
See application file for complete search history.

(56) References Cited

U.S. PATENT DOCUMENTS

| | | | |
|---|---|---|---|
| 2002/0039599 A1* | 4/2002 | Lin | A61B 5/412 |
| | | | 424/558 |
| 2005/0054724 A1 | 3/2005 | Mustad et al. | |
| 2007/0292501 A1 | 12/2007 | Udell | |
| 2011/0294876 A1* | 12/2011 | Kuper | A23G 4/06 |
| | | | 514/465 |

FOREIGN PATENT DOCUMENTS

| | | | |
|---|---|---|---|
| WO | WO 2005070404 | * | 8/2005 |
| WO | WO 2007143652 | * | 12/2007 |

OTHER PUBLICATIONS

Advertisement—www.intelligentnutrients.com Intellimune the Seeds of Change (attached hereto for reference).
Ashok, Dapkupar Wankhar, Wankupar Wankhar, R Sheeladevi, Neurobehavioral Changes and Activation of Neurodegenerative Apoptosis on Long-term Consumption of Aspartame in the Rat Brain, Journal of Nutrition & Intermediary Metabolism 2 (2015) 76-85.
Bjornsson Einar S. ; Hepatotoxicity by Drugs the Most Common Implicated Agents; International Journal of Molecular Sciences: pp. 1,2,3,4,6,7 Feb. 26, 2016.
Brown, Charles H.; Drug Induced Serotonin Syndrome;US Pharm. 2010; p. 3; Nov. 17, 2010.
Chassaing Benoit, Omry Koren, Julia Goodrich, Angela Poole; Shanthi Srinivasan, Ruth E. Ley, and Andrew T. Gewirtz; Nature. Mar. 5, 2015; pp. 1, 2.
Chokawala Krutika, Stevens, Lee; Antipsychotic Medications;The National Library of Medicine, National Institutes of Health. StatPearls; StatPearls Publishing; Jan. 2021; pp. 3.
Cisapride; National Institutes of Health; MedlinePlus; pp. 1,2 Nov. 15, 2017.
Finn Andrew PharmD, Collins Jason PharmD, Voyksner Robert PhD, Lindley Celeste PharmD Bioavailability and Metabolism of Prochlorperazine Administered via the Buccal and Oral delivery Route, J Clin Pharmacol. Dec. 2005 45(12): 1383-90.
Francino, M. P.; Antibiotics and the Human Gut Microbiome: Dysbioses and Accu-mulation of Resistances;Francino MP (2016) Antibiotics and the Human Gut Microbi-ome: Dysbioses and Accu-mulation of Resistances, Frontiers in Microbiology Jan. 2016 vol. 6 pp. 1-11.

(Continued)

*Primary Examiner* — David J Blanchard
*Assistant Examiner* — Sarah J Chickos
(74) *Attorney, Agent, or Firm* — David P. Lhota, Esq.; Lhota & Associates, P.A.

(57) ABSTRACT

A nutritional and cosmetic system, product, and method for improving the health, growth and appearance of hair, skin, nails, and body, including the principle active ingredients of lipids and vitamins, including vitamin C, and biotin and minerals, including phosphorus, wherein the product is applied topically to the skin, hair, nails and, or body while also being ingested and, or injected. A vanilla or other scented extract may be added to enhance the pleasant scent of the product and system. The nutritional and cosmetic product and system may be applied to the hair directly or in a shampoo, to the face, body, and nails, ingested, and or applied topically to the hair, skin, nails and or body.

15 Claims, 13 Drawing Sheets

(56) References Cited

OTHER PUBLICATIONS

Gupta Ramesh C, Ida R. Miller Mukherjee, Robin B. Doss, Jitendra K Malik, Dejan Milatovic; Organophosphates and Carbamates; Reproductive and Developmental Toxicology (Second Edition) 2017, pp. 609-631.
Herman Timothy F, Santos Cynthia; First Pass Effect; The National Library of Medicine, National Institutes of Health: StatPearls Publishing; Jan. 2021.
Johansen J D, Frosch P J, Svedman C, Anderson K E, Bruze M, Pirker C, Menne T; Hydroxyisohexyl 3 cyclohexene carboxaldehyde (Lyral); Quantitive As-pects and Risk Assessment of an important fragrance allergen, Contact Dermatitis Jun. 2003; 48(6):310-6.
Journal of the American College of Toxicology; Sodium Lauryl Sulfate; Final Report on the Safety Assessment of Sodium Laurel Sulfate and Ammonium Laurel Sulfate; 1983; p. 175.
Khan, Tariq Jamal, Hasan Mohammad Nihal, Azhar, Esam I, Yashir, Mu-Hammad; Association of Gut Dysbiosis With Intestinal Metabolites in Response to An-tibiotic Treatment; Human Microbiome Journal 11 (2019).
Kobylewski Sarah, Jacobson, Michael F; Toxicology of Food Dyes; Int J Oc-cup Environ Health. Jul.-Sep. 2012 (Red 40, Blue 1 and other US approved food dyes have been scientifically tested).
Lynch, Shalini S., PharmD; Genetic Makeup and Response to Drugs; Merck Manual Professional Version; Aug. 2019.
Marcelino Gabriela, Priscila Aiko Hiane , Karine De Cássia Freitas, Lidiani Figueiredo Santana, Arnildo Pott, Juliana Rodrigues Dona-Don and Rita De Cássia Avellaneda Guimaraes, Effect of Olive Oil and its Minor Component on Cardiovascular Diseases, Inflammation, and Gut Microbiota, Nutrients 2019, 11, 1826.
Merck Manual, Seventeenth Edition; p. 152.
Mesalamine; drugs.com.
Mizuno, Shinta, Keiko Ono, Yohei Mikami, Makoto Naganuma, Tomohiro Fukuda, Kazuhiro Minami, Tatsuhiro Masaoka, Soichiro Terada. Takeshi Yoshida, Keiichiro Saigusa, Norimichi 5-Amino salicylic acid intolerance in patients with ulcerative colitis, Dept. of Internal Medicine, Keio University.
Pancrelipase; MedlinePlus May 15, 2016.
Pancreatic Enzymes Wikipedia Aug. 23, 2021 (Medication is prescribed via the oral route and cautions regarding proven adverse effects at high doses over a long period of time).
Peng Luying, Zhenjuan He, Wei Chen, Ian R Holzman & Jing Lin; Pediatric Research 61, 37-41 (2007);pp. 1,2 12.
Perez-Burillo S., D. Hinojosa-Nogueira, S. Pastoriza , J.A. Rufian-Henares; Plant Extracts as Natural Modulators of Gut Microbiota Community Struc-ture and Functionality; Heliyon 6 (2020).
Pharmacokinetics; columbia.edu, pp. 33, 41.
Pharmacology Education Project; Individual Variation in Drug Response, pp. 1.
Shastry, B. S.; Pharmacogenetics and the concept of individualized medicine; Heli-yon 6 (2020); p. 16.
Shyian D, Oavilova, A Bondareva, O Prykhodko; Organometric Changes in Thymus Under the Influence of Propylene Glycol; Georgian Med News. Jun. 2019 (291) 112-117.
Le Jennifer, PharmD; Merck Manual Professional Version; Oct. 2020.
Merck Manual, Seventeenth Edition 1999; p. 2558.
Weng Xinchu, Zhuoting Yun, Chenxiao Zhang; Comparison of the Character-istics of Two Kinds of Tea Seed Oils: Oil-tea Seed Oil and Green-Tea Seed Oil; Journal of Food Studies vol.7, No. 1 (2018).
Merck Manual, Seventeenth Edition 1999; p. 2559.
Merck Manual, Seventeenth Edition 1999; p. 2570.
Merck Manual, Seventeenth Edition 1999; p. 2582.
Merck Manual, Seventeenth Edition 1999; p. 2592.
Merck Manual, Seventeenth Edition 1999; p. 2595.
Merck Manual, Seventeenth Edition 1999; p. 2597.
Pharmacology Education Project; Individual Variation in Drug Response, p. 2.
Pharmacology Education Project; Individual Variation in Drug Response, p. 3.
Pharmacology Education Project; Individual Variation in Drug Response, p. 5.
Ball, A. P.; Gray, J. A. & Murdoch, J. McM; The Natural Penicillins—Benzylpenicillin (Penicillin G) and Phenoxymethylpenicillin (Penicillin V). Antibacterial Drugs Today pp. 6-18.
D S Bansi, D S, Price A, Russell, C, Sarner M; Case Report; Fibrosing colonopathy in an adult owing to over use of pancreatic enzyme supplements; gut.bmj.com; Department of Gastroenterology, The Middlesex Hospital, Mortimer Street, London, UK.
Columbia.edu; Pharmacokinetics; p. 41.(Kinetics Following a Single Drug Dose).
FitzSimmons Stacey C, Burkhart Greg A, Borowitz Drucy, Grand Richard J, Hammer-strom Thomas, Durie Peter R, Lloyd-Still John D, Lowenfels Robert D; High-Dose Pancreatic Enzymyme Supplements and Fibrosing Colonopathy in Children with Cystic Fibrosis, The New England Journal of Medicine, vol. 336, No. 18 pp. 1283-1289.
drugs.com; Drug Interactions Between Cipro XR and Fluoxetine; (Fluoxetine combined with Cipro can induce serious arrhythmias).
drugs.com; Pancreatin; (A medication associated with adverse side effects).
Juhaimi Fahad Al, Özcan Mehmet Musa, Ghafoor Kashif, Babiker Elfadl E., and Hussain Shahzad; Comparison of cold-pressing and soxhlet extraction systems for bi-oactive compounds, antioxidant properties, polyphenols, fatty acids and tocopherols in eight nut oils, J Food Sci Technol (Aug. 2018) 55(8):3163-3173.
Li Jing, Wang Xuling, Zhang Ting, Wang Chunling, Huang Zhenjun; A review on Phospholipids and Their Main Applications in Drug Delivery Systems; Asian Journal of Pharmaceutical Sciences 10 (2015) 81-98.
Martins, Marcia S, Ferreira Marta S. , Almeida Isabel F. and Sousa, Emília; Cosmetics; Occurrence of Allergens in Cosmetics for Sensitive Skin; Laboratory of Organic and Pharmaceutical Chemistry, Department of Chemical Sciences, Faculty of Pharmacy, University of Porto, 4050-313 Porto, Portugal.
Medline; Mesalamine; (Do not double dose).
Suraev Anastasia, Benson Melissa J., Martin Lewis, Lintzeris Nicholas, McGregor Iain S.; Determination of contaminants in artisanal cannabis products used for childhood epilepsy in the Australian community: A sub-analysis of the 'Pelican' study, Epilepsy & Behavior 127 (2022) 108496.
Samsuri Azrul Hisyam, Ang May Yen, Yeaw Shean; Optimization of Residual Hexane in Edible Oils Analysis Using Static Headspace Gas Chromatography; Hindawi International Journal of Analytical Chemistry vol. 2021, Article ID 1941336, 6 pages.
Tariq, Rayan A., Vashisht, Rishik, Sinha, Ankur, Scherbak, Yevgeniya; Medication Dispensing Errors and Prevention; NCBI Bookshelf; StatPearls Publishing L.L.C. 2022.(Errors in medication dispensing).
Viviers Hendrick Jacobus, Petzer Anel, Gordon Richard; An assessment of solvent res-idue contaminants related to cannabis-based products in the South African market; Journal of Cannabis Research (2022) 4:19.
Volpi-Abadie, Jaqueline, Kaye, Adam M., Kaye, Alan David; Seotonin Syndrome; Ochsner J; 2013. Table 4; (A potentially life threatening syndrome that can be induced by the combination of serotonergic drugs).

\* cited by examiner

*FIG. 1*
*Method Action Chart*

The Nutritional Cosmetic System

*A Therapeutic System For Aesthetic Enhancement*

*The nutritional cosmetic system is an interactive system of integral nutrient and method components that when implemented, co-act in a complementary mode, rendering a dynamic process for anti-aging and aesthetic enhancements of the hair, skin and nails.*

*FIG. 2*
*The Nutritional Cosmetic System*
*Overview*

*FIG. 3*
*The Nutrient System*

*An interactive nutrient system primarily comprising plant food sourced nutrient components, supplemented with additional complementary nutrients.*

*The nutrient system implements interdependent, plant sourced nutrient components, blended with the addition of interdependent supplemental nutrients relevant to the health and enhancement of the hair, skin and nails, the modification of the dose levels of the nutrients, variations of the ingredient components, comprising organic, raw and whole form variations and the phosphorous nutrient system component, which results in a highly bioactive, bioavailable and biocompatible nutrient system which induces individual and collective reactions and interactions of the inherent bioactive compounds, producing catalytic, complementary and potentized action of the formula;*

*a) The Relevant Supplemental Nutrients*

*The nutrient system comprises the addition of supplemental of nutrients which have demonstrated to perform optimally, such as B vitamins, comprising biotin and minerals such as silica and phosphorous, resulting in enhanced therapeutic and aesthetic effects to the hair, skin and nails.*

+

*b) The Relevant Plant Sourced Nutrients*

*The formula principally comprises plant food sourced extracts such as flax seed oil and other relevant extracts.*

*The bioactive compounds inherent to the selected extracts demonstrate an exceptional level of biological relevance to the hair, skin and nails, resulting in enhanced therapeutic and aesthetic effects to the hair, skin and nails.*

+

*c) The Interdependent Supplemental Nutrients*

*Interdependent nutrients such as calcium, magnesium and Vitamin D are required for phosphorous metabolism and perform as catalysts, activators, etc., inducing complementary interactions of the nutrient components.*

+

*d) The Interdependent Plant Sourced Nutrients*

*Although plant food sourced extracts comprise a mixture of nutrients, combined food based, plant sourced extracts comprising significant and higher levels of deliberately blended interdependent nutrients, demonstrate a higher level of synergistic bioactivity and complementary interactions.*

*Example; Broccoli and almond extracts are utilized for plant sourced calcium, which is an essential, interdependent nutrient for the utilization of plant sourced phosphorus of the formula.*

*e) Multi Purpose Action Of The Nutrient Components*

*Implementing a single formula of nutrient components relevant to the hair, skin and nails for multi purpose therapeutic action;*

*Example 1; Vitamin c performs as an essential nutrient to nourish and regenerate the hair, skin and nails, as an effective nutrient for UV protection and as an effective antioxidant preservative.*

*Example 2; The mineral phosphorous performs as a catalyst within the formula, as a necessary nutrient to regenerate the hair, skin and nails and as an effective, therapeutic nutrient for wound, burn and scar therapy of the skin.*

✢

*f) The Customized Formulations*

*1) Customized Variation of the Nutrient Components*

*A customized variation of the nutrient components should be evaluated such as for those individuals who are sensitized to a requisite ingredient component;*

*Example; Individuals who are sensitized to an ingredient component of the formula such as rice bran oil and who require wound, scar or burn therapy of the skin; a customization formulation should be indicated as to substitute the rice bran component for a natural lecithin ingredient component that comprises significant and higher levels of the mineral phosphorous, which is a necessary component for the performance and the action of the formula and is also an essential nutrient component for wound and burn therapy.*

✢

*g) Potency Management*

*Managing the potency of the nutrient system through modifications of the nutrient component levels and form*

*The nutrient system primarily resources the natural and inherent, lower nutrient levels of the plant extracts, which thereafter, are potentized by the application techniques. However, modification of nutrient levels and form should be evaluated for the customized potency applications.*

*Example 1; phosphorous;*

*The proprietary phosphorous formula is effective for the initial and recovery phases of burn therapy. Modification of the phosphorous nutrient system level and form, according to the homeopathic dilution, should be evaluated for wound, scar and burn therapy.*

FIG. 3 (continued)

*Example 2; Vitamin C;*

*As a divergence of the minimum effective dose level, vitamin C may be modified to a higher dose level an effective nutrient and as a safely tolerated, therapeutic dose level for skin wound, burn and scar therapy.*

*As a single nutrient, Vitamin C may be potentized modifying the therapeutic dose level, or, according to the homeopathic dilution form and may be further potentized by the application techniques, or, the lower level dose form may be potentized by the application techniques alone.*

*Example 3;*
*The Homeopathic Dilution;*

*Maximum potentization of the nutrients is achieved through the homeopathic dilution form. The homeopathic dilution for potentization purposes should be evaluated, especially for those individuals who require a maximum, bio-affecting, potentization form, utilized for targeted cosmetic enhancements or wounds and scars associated with major burn therapy.*

*The homeopathic dilution form may be implemented for the orally administered application, the topical and transdermal applications or the variation of the application techniques, such as the injection method techniques.*

*Example 4;*
*The Formulation Mixtures*

*The instant invention may comprise formulation mixtures, such as a mixture of the nutrient system base form and a homeopathic dilution form. The formulation mixtures comprising the base form and the homeopathic dilution induce accelerative action of the base form nutrient components and may be implemented for the major burn therapies as a rapid-acting therapeutic.*

*FIG. 4*
The Phosphorous Nutrient System
*A Nutrient Catalyst*

*The phosphorous nutrient system comprises plant and seed extracts of higher levels of phosphorous, the addition of natural sources of phosphorous, such as phospholipids, the addition of complementary nutrients necessary for phosphorous metabolism and plant sources of these necessary and complementary nutrients. The phosphorous nutrient system demonstrates catalytic action and activates potentiation of the formula's bioactive ingredient components.* a) *plant sources and seed extracts of higher levels of phosphorous.*

+ b) *the addition of phosphorous sources; phospholipids, a trace mineral source and the pure mineral form.*

+ c) *interdependent supplemental nutrients that are necessary for phosphorous metabolism.*

+ d) *plant sources and seed extracts comprising higher levels of interdependent nutrients.*

+ e) *the interaction of the phosphorus formula with the bioactive components of the principal formula.*

↓ f) *Potentiation*

*The phosphorous sources perform as catalysts and nutrient potentiators, interacting with the remaining bioactive ingredient components of the formula, inducing an efficient level of intracellular absorption of the nutritive components, activating potentization, furthermore, producing accelerative action of the nutrient system.*

+

FIG. 5
The Delivery Methods

*The Application Techniques*

*The application techniques are implemented as delivery methods of dispensation, activation, potentization and methods of potency management for the designated applications and method techniques thereof.*

*a) The Single Formula Method*

*A single formula implemented for both topical and orally administered applications. The single formula is simultaneously ingested and applied topically to hair, skin and nails as a single formula dispensation method technique and is also implemented according to the variations of the application techniques.*

+

*b) The Dual Application Delivery Method*

*A combined and simultaneous delivery method incorporating an orally administered application with a topical and transdermal application.*

*c) The Orally Administered Application*

*The orally administered application is metabolized internally through the enteral route, subsequently inducing systemic action, resulting in therapeutic and aesthetic enhancements of the hair, skin and nails.*

+

*d) The Topical Application*

*Topical application to the hair, skin and nails induces a local effect of therapeutic action resulting in aesthetic enhancements of the hair, skin and nails.*

+

*e) The Transdermal Nutrient Delivery Method*

*An Effective Approach To Cosmetic Enhancement*

*Topical application of the bio-affecting nutrients to the skin produces the transdermal effect;*

*The transdermal application promotes efficient absorption of nutrients; The topical application of the bioactive and bioavailable nutrient compounds, activates the transdermal diffusion effect; nutrients are absorbed by the tissues and cells of the epidermis and dermis, inducing a local effect which nourishes and regenerates the skin. Thereupon, the bioactive nutrients are absorbed and metabolized through the transdermal delivery route. Thereafter, the nutrients are further metabolized, inducing systemic effects.*

*f) The Variations Of The Application Techniques*
*The Injection Method Technique*

*Example 1) the injection method + orally administered application,*
*2) injection method + topical and transdermal application,*
*3) injection method + orally administered application + topical and transdermal application.*

*Examples may be modified and may integrate multiple delivery routes of administration, determined by the designated applications.*

+

*g) Potency Management;*

*h) The Application Techniques*
*Managing the potency of the nutrient system through the application techniques*

*The application techniques may be skillfully executed to achieve customized potency management of the nutrient system, evaluating the nutrient components form and levels, the successive applications of the interval dose regimen and the routes of administration as prescribed according to the designated applications.*

*Maximum potentization is achieved, utilizing the inherent, lower level nutrient form or the maximum potency forms of the nutrient components, implementing the application techniques through multiple delivery routes, which induce multiple metabolic interactions (the multi action processes).*

*(FIG. 5h-1) As an example of a designated application for specific cosmetic enhancements, such as a targeted area of a wrinkle of the facial skin, implementing the dual application delivery method, utilizing the base form of the nutrient system and; the injection method technique, utilizing the potentized homeopathic dilution form, activates maximum potentization of the nutrient system action;*

*(FIG. 5h-1)*

*Targeted Area Cosmetic Enhancements Of A Wrinkle of The Facial Skin;*

*a) The orally administered application of the base form of the nutrient system*

*The enteral route of administration → systemic action*

+

*b) The topical application of the base form of the nutrient system*
*(the homeopathic form may also be applied topically)*

FIG. 5 (continued)

*Topical* → *local effect*

↓

*The transdermal diffusion effect*

↓

*The transdermal route of administration* → *systemic action*

+

*c) The cutaneous injection method of the homeopathic dilution* → *local effect*

↓

*The transdermal diffusion effect*

↓

*The transdermal route of administration* → *systemic action*

↓

*d) Multiple pathway activation* → *multiple metabolic interactions (the multi action processes)*

↓

*f) Maximum potentization*

↓

*i) The Interval Nutrient Dose Regimen*

*Implementing an interval dose regimen of the inherent, lower level nutrient system through multiple delivery routes, induces a higher level of bioactivity and bioavailability of the nutrient system, activating potentization.*

*Examples of interval nutrient dose level regimens according to the aforementioned designated application as exhibited in (FIG. 5h-1);*

*A targeted area, specific therapeutic and cosmetic enhancement of a wrinkle of the facial skin;*

FIG. 5 (continued)

*Example 1 Specific Therapeutic and Cosmetic Enhancement of a Facial Wrinkle;*

9 am) *a simultaneous subcutaneous injection of the homeopathic dilution of the nutrient system into the targeted area wrinkle site + a topical application of the base form of the nutrient system onto the targeted area wrinkle site + an orally administered application of the base form of the nutrient system*

12 pm) *a simultaneous topical application of the homeopathic dilution form + an orally administered application of the base form of the nutrient system.*

9 pm) *a simultaneous topical application of the base form + an orally administered application of the base form of the nutrient system.*

*Example 2 Specific Therapeutic and Cosmetic Enhancement of a Facial Wrinkle;*

9 am) *a simultaneous subcutaneous injection of the homeopathic dilution of the nutrient system into the targeted area wrinkle site + a topical application of the homeopathic dilution of the nutrient system onto the targeted area wrinkle site + an orally administered application of the base form of the nutrient system*

12 pm) *a simultaneous topical application of the homeopathic dilution of the nutrient system onto the targeted area wrinkle site + an orally administered application of the base form of the nutrient system.*

9 pm) *a simultaneous topical application of the base form of the nutrient system onto the targeted area wrinkle site + an orally administered application of the base form of the nutrient system.*

FIG. 6
The System Action

The Multi Action Processes

The nutritional cosmetic system is an interactive delivery system of integral nutrient and method components that when implemented simultaneously, co-act in a complementary mode, inducing multiple metabolic interactions, rendering a dynamic process for anti-aging and aesthetic enhancements of the hair, skin and nails.

a) The Nutrient System Action

The multi action processes are activated by the nutrient system in coaction with the application techniques. The natural and inherent, lower level nutrient components are activated by the application techniques and may include the addition of method action from the modification of the nutrient component levels and form and from a variation of the application techniques.

The natural and inherent, lower level nutrient components induce individual and collective reactions and interactions, producing catalytic, complementary and potentized action. The nutrient components are further potentized by the subtle, physiological interactions induced by the collaboration of the multiple nutrient routes of administration (the application techniques), resulting in multiple metabolic interactions (the multi-action processes).

+ b) A Variation of The Nutrient System Action
The Homeopathic Dilution

May include a variation of the action of the nutrient system, such as the potentized action from the homeopathic dilution form.
In co-action with the application techniques, the homeopathic dilution of the base form of the nutrient system activates maximum potentization of the bio-affecting components of the nutrient system.

+

The Potentized Homeopathic Dilution And The Base Form Of The Nutrient System

The potentized homeopathic dilution activates the metabolic process, inducing a synergistic collaboration between the potentized homeopathic dilution and the base form of the nutrient system resulting in a more efficient level of bioactivity, bioavailability and biocompatibility of the base form nutrient system.

For optimal potency, it is recommended to implement a dual application, incorporating the base form of the nutrient system, simultaneously with the homeopathic applications or following the homeopathic applications.

+

The Formulation Mixtures

The instant invention may comprise formulation mixtures, such as a mixture of the nutrient system base form and a homeopathic dilution form. The formulation mixtures comprising the base form and the homeopathic dilution induce accelerative action of the base form nutrient components and may be implemented for the major burn therapies as a rapid-acting therapeutic.

FIG. 6 (continued)

+ c) The Dual Application Delivery Method Action the orally administered action + the topical application and the transdermal nutrient delivery method application The dual application delivery method is a maximum potentization technique. The subtle, physiological interactions induced by the collaboration of the bioactive nutrient components, through multiple delivery routes, induces multiple metabolic interactions, activating potentization;

↓ d) Complementary Action
The dual application delivery method produces complementary, physiological interactions;

The Orally Administered Action
1) The orally administered application action is metabolized internally through the enteral route of administration, producing therapeutic action outwardly.

FIG. 6d-1
enteral metabolism action

------↑------ the epidermis
------↑------ the dermis, veins

The Topical and Transdermal Application Action
2) The topical application nutrient action is absorbed and diffused through the transdermal route of administration and metabolized inwardly.

The topical application of bioactive and bioavailable nutrient compounds, absorbed by the tissues and cells of the epidermis and dermis, induces a local effect that nourishes and regenerates the skin. Thereupon, the nutrients are absorbed into the bloodstream by the veins of the dermis through the transdermal delivery route. Thereafter, the nutrients are further metabolized, inducing systemic effects.

FIG. 6d-2
cutaneous metabolism action

------↓------ the epidermis
------↓------ the dermis, veins

+ e) Uniformity of Action

A single formula simultaneously dispensed through multiple delivery routes, maintains optimal levels of synergistic bioactivity of the nutritive components, resulting in uniformity of action of the formula's bio-affecting ingredient components, activating potentization;

FIG. 6 (continued)

*FIG. 6e-1*
*orally administered application;*

*enteral route of administration* → systemic action

*FIG. 6e-2*
*topical application;*

*topical* → local effect

↓ the transdermal diffusion effect

↓

*transdermal route of administration* → systemic action

↓

*multiple pathway activation* → *multiple metabolic interactions (the multi action processes)*

+

*f) A Variation of The Dual Application Delivery Method Action*

*Example; a variation technique which integrates a cutaneous injection;*

*the cutaneous injection + the orally administered application + the topical and transdermal application;*

*This unique method variation system integrates the orally administered method action + the topical and transdermal method action (the dual application delivery method) + the injection method action, metabolized through multiple delivery routes, which induces multiple metabolic interactions, activating maximum potentization.*

↓

*g) Potentization*
*The vigorous synergistic action induced from the co-action of the bioactive nutrient system and the application techniques, activates potentization.*

↓

*h) Accelerative Action*
*The potentized action activated by the co-action of the bioactive nutrient components and the application techniques, induces accelerative action of the formula's bioactive nutrient components.*

↓

FIG. 7
The Therapeutic Action
The Sequential Process of Therapeutic Action i) Therapeutic Action
The complementary interactions produced by the application techniques, in co-action with the bioactive nutrient components, activates potentized and accelerative action, which induces therapeutic action of the nourishing bioactive nutrient components.

j) Therapeutic Effects
Therapeutic regeneration and restoration of the hair, skin and nails.

k) Aesthetic Enhancements
Enhanced and refined visual appearance and texture of the hair, skin and nails.

l) Progressive Aesthetic Enhancements
Successive applications of the nutritional cosmetic system demonstrate progressive, anti-aging and refined enhancements of the hair, skin and nails.

FIG. 8
Juliana Konzny
Copyright © 2010-2013

NUTRITIONAL AND COSMETIC PRODUCT, SYSTEM AND METHOD FOR USE

CROSS REFERENCE TO RELATED APPLICATIONS

This application is a continuation-in-part of U.S. patent application Ser. No. 13/080,909 filed Apr. 6, 2011, which claims the benefit of provisional patent application Ser. No. 61/341,872 filed Apr. 6, 2010.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights rights whatsoever.

BACKGROUND OF THE INVENTION

Field of the Invention

This invention relates to cosmetic health and body enhancement compositions and methods, implementing potentiated compositions and multiple and simultaneous delivery routes, thus providing integral methods to achieve a dynamically potentized nutrient system, resulting in permanent aesthetic enhancements of the hair, skin, nails and body.

THE BACKGROUND

Approaches to improving the health and appearance of the hair, skin and nails have been attempted, implementing separate applications of various hair, skin and nails preparations, such as synthetically based topical cosmetic preparations, ingestible nutrient supplements or through the implementation of a combination of these dissimilar preparations, which have demonstrated to be primarily ineffective, bio incompatible and potentially toxic to the human organism.

Such preparations do not sufficiently or appropriately address the needs within the industry due to temporary results and potentially adverse biological reactions.

Synthetically based cosmetic products on the market, such as those that comprise sodium lauryl sulfate (CDC; NIOSH) or propylene glycol, have proven that they are inappropriate for sensitive skin and can induce irritations (Jasser et al). Facial, body creams and lotions apply a superficial layer of lubrication over the skin to temporarily moisturize it while the preparation remains on the skin, however, demonstrate to be deficient in promoting permanent, therapeutic and aesthetic results.

Methods to potentiate ingestible nutrient substances to achieve accelerated therapeutic effects have been attempted, implementing higher nutrient levels and/or higher volume doses of an ingestible nutrient supplement, dispensed through an individual route of administration, such as the enteral route. This process may induce adverse side effects, such as nutrient level overload (overdose). (Bailey et al. 2011).

Approximately 60,000 occurrences of vitamin toxicity are reported annually to US poison control centers. (Rosenbloom; 2017).

Higher intakes of micronutrients have demonstrated to induce adverse effects, even at standard suggested doses.

Ingesting multi vitamin and multi mineral supplements (MVMs) can elevate risks of nutrient overload, especially when more than a basic "once daily" supplement that provides 100% of the daily value (DV) of nutrients is ingested. Complicating the issue is the fact that dietary supplements are 9-ot required to be standardized in the US. There is no standard or regulatory definition for MVMs, such as to what they must comprise or at what levels. It is left to the discretion of the MVMs manufacturer. (NIH; Dietary Guidelines for Americans 2015-2020).

A further example of a potency method fox therapeutic or cosmetic health benefits includes ingesting higher nutrient levels or volume levels of fatty acids supplements (PUFAs).

Studies confirm that macronutrient overload, such as by excessive intake of fatty acids, can also induce adverse effects. (H. Qin et al.)

Albeit, scientific studies also demonstrate the benefits of nutrient supplementation for general overall health and treatment of disease.

Emerging evidence suggests that complimentary phosphorus supplementation may benefit the effectiveness of calcium in reducing the risk of developing disease. (Heaney et al. 2003). Most dietary supplements do not contain significant amount phosphorus and the contribution of dietary supplements to phosphorus is low. (Bailey et al. 2011).

The implementation of nutrient supplements for therapeutic and cosmetic enhancement has demonstrated to be beneficial, however, based on factors such as age and health profile, some individuals do not maintain the required daily intakes.

Reports suggests that most individuals can acquire all of the necessary vitamins and minerals through a healthy eating pattern of nutrient dense foods, although consuming multi vitamin and multi mineral supplements (MVMs) increase overall nutrient intake and helps individuals to achieve recommended amount levels of vitamins and minerals when they cannot or do not ingest them from food alone. (NIH; Dietary Guidelines for Americans 2015-2020).

Campaigns to increase intake of food nutrients for health benefits have demonstrated to be unproductive.

Despite the campaigns promoting increase consumption of fruits and vegetables for overall health, most adults are still not consuming adequate amounts for health benefits. (Guenther et. al.)

In addition to the aforementioned risks associated with high nutrient/volume level induced overload, general guidelines for nutritional supplements and food nutrient dosage protocols remain difficult to quantitate and confusing for the end user, therefore potentially ineffective and as well as unsafe.

Nutrient level assessments remain difficult to quantitate due to conditions, such as the variations of the health profiles of end users. Moreover, the end user might be reluctant to ingest high nutrient level supplements for fear of nutrient overdose. The end user may also be disinclined to habitual ingestion of higher volume amounts of food based nutrients, especially those end users who are conscious about body fat and weight management, in addition to the tedious routine required to ingest such suggested amounts to induce beneficial health effects.

U.S. Pat. No. 7,759,507 provides an ingestible lipid system product of specific ratios of omegas, comprised within a pharmaceutical composition for improving glucose tolerance and insulin sensitivity and for reducing the risk of vascular disease.

Mustad et al., (Mustad), discloses a lipid system product containing flax oil and vitamin C, adapted for improving glucose tolerance and insulin sensitivity and for reducing the risk of vascular disease. U.S. Pat. No. 7,759,507 also discloses the method of a lipid nutrient system comprising synthetic ingredients, administered through the enteral mute.

However, the system does not provide a topical and ingestible product, comprising biologically relevant and principally implemented nutrients, which have been proven to promote healthier hair, skin and nails, such as silica.

U.S. Pat. No. 7,759,507 is a complex formula, comprising synthetic additives and utilizing higher levels of the nutrient components;

Additionally, U.S. Pat. No. 7,759,507 does not disclose a system implementing a minimum effective dose concept, such as the principal utilization of the inherent, lower nutrient levels of plant based sources, nor discloses a system for retaining the inherent nature of the plant extracts, implementing natural methods of derivation, extraction, processing, manufacturing and preservation of naturally sourced ingredient components.

U.S. Pat. No. 7,759,507 does not disclose the utilization of low level nutrient formulations and varying methods of use, such as implementing a dilution form and a simultaneous, dual application delivery method, as designated applications, such as for skin wound, burn and scar therapy.

The U.S. Pat. No. 7,759,507 product and system does not disclose methods to administer at lower nutrient levels to avoid potential nutrient overload, nor does it disclose a natural nutrient system.

In contrast, the nutritional cosmetic system invention is for according to a minimum effective dose concept; the primary utilization of the inherent lower nutrient levels of a variety of plant food groups, supplemented with lower nutrient levels.

Furthermore, is deliberately formulated to target cosmetic enhancements, implementing a system of naturally inherent nutrient components, biologically relevant to enhance the health and appearance of hair, skin and nails of humans of varying ages and animals alike.

As an additional example of a product and system for therapeutic health benefits, US 2002/003959, discloses therapeutic methods of diagnosing and treating small intestinal bacterial overgrowth (SIBO) and SIBO related conditions to the intestinal system.

US 2002/003959 discloses in paragraph [0160]; an emulsifying and suspending agent that is acceptable for human consumption, including sodium lauryl sulfate and carboxymethylcellulose.

Sodium lauryl sulfate has been reported to cause acute digestive symptoms when ingested (CDC; NIOSH).

A 2015 study reported that dietary emulsifiers, such as carboxymethylcellulose, alter gut microbiota and cause numerous adverse health affects. (Chasssaing et al).

Antibiotics [0193] are known to injure delicate intestinal flora and cause dysbiosis.

Paragraph [0167] discloses a higher volume level dose of a lipid in a load dependent method. Paragraph [0156] discloses that fatty acids contemplated by the invention include those having between 4 and 24 carbon atoms.

A 1990 study on nutrient interrelationships reports that a loss of homeostatic equilibrium between nutrients caused by excess intake of a single nutrient may have an adverse effect upon health. As an example, excess intake of a single element, such as zinc, can decrease or depress the intestinal absorption of another element, such as copper. (Watts).

A 2018 article referencing a scientific study and review on the role of dietary minerals on microbiota and disease (Lopez, Skaar), reported that dietary metal deficiency or excess can alter microbiota and decrease resistance to *Clostridium difficile* infection. (Prados).

A 2007 pediatric research study reports that overproduction and accumulation of short chain fatty acids in the bowel may be toxic to the intestinal mucosa and may play a role in the pathogenesis of neonatal necrotizing enterocolitis. (Peng et al).

US 2002/0039599 discloses preferred embodiments that lack a natural, a low nutrient/volume dose level nutrient system composition for simultaneous administration to multiple delivery routes, as a safe and healthy approach to therapeutic benefits.

Attempts at general health and cosmetic enhancement include methods utilizing natural substances, such as a plant seed extracts, administered through the enteral route and including the option to administer topically (Intellimmune). However, the product and system does not disclose methods to administer at lower nutrient levels to avoid potential nutrient overload, nor does the product and system disclose methods of a specific, simultaneous targeted delivery approach. Implementing-the aforementioned collective approaches, in particularly, if administered simultaneously through multiple routes, would likely lead to nutrient overload and proven adverse effects, such as cell injury, gastrointestinal irritation and microbiota alterations.

Attempts at targeted cosmetic enhancement, such as to a facial wrinkle, include topical delivery of synthetically based preparations. However, synthetic components demonstrate limited bioavailability and diffusion to subcutaneous target cells and inappreciable permanent therapeutic and aesthetic results. Further attempts at targeted cosmetic enhancement include implementing synthetically based composition injections and may induce adverse reactions due to potentially toxic substances utilized.

As a method of targeted wrinkle enhancement, a cosmetic injectable implements a pharmaceutical grade neuro toxin extract. The preparation comprising the toxin extract paralyzes the injection site muscles by blocking the release of neurotransmitter impulses to the muscles. It has been reported that this product and system can induce adverse side effects from flu like symptoms drooping eyelids to the more serious organ system dysfunction. Inflammation has also been reported as a side effect. (drugs.com; Botox side effects). Reports indicate that the product and system demonstrates temporarily diminished wrinkle results. (Medline; botox). The onabotulinum toxin A injectable system has not sufficiently or appropriately addressed the needs of the industry due to the potentially adverse affects and inappreciable permanent therapeutic or cosmetic restoration effects.

Skin burns can be caused by free radical (or oxygen radical) affects from prolonged sun exposure (or solar radiation) and can induce DNA strand breaks and damage to the skin. (Steinberg et al.) Therapeutic treatment for skin and tissue damage due to burns, such as from extreme heat have been attempted according to a critical care therapeutic protocol. Hypophosphatemia (decreased plasma and/or intracellular phosphate concentration) typically occurs as a result of major burns to the skin tissues, cartilage and/or bones (The Merck Manual).

Scars to the skin also develop as a result of major burns. Treatment protocols can typically induce complications as a result of mismanaged phosphate repletion protocols and improper wound healing.

Radiation exposures from modern technological devices, such as cell phones and computers can also induce thermal heating and cause burns that lead to tissue damage (American Cancer Society). Cell phone radiation has been scientifically studied and demonstrated to produce radicals and cause DNA damage. (Lai et al) (PSRAST).

Additionally, radiation therapy can cause DNA damage to skin and tissue burns (or radiation dermatitis).

Lipids are integral components of skin and hair development and function. (LEE et al).

Oxygen radicals can also damage cellular components, such as lipids. Oxygen radicals can oxidize lipid molecules to generate intermediates that react with DNA. The polyunsaturated fatty acid residues of phospholipids are extremely sensitive to oxidation. The high concentration of polyunsaturated fatty acids in phospholipids makes them prime targets for reaction with oxidizing agents. Linoleic acid is the most common polyunsaturated fatty acid within cells. (Marriott). It is estimated that 60 molecules of linoleic acid are consumed per oxidant that reacts with the phospholipid bilayer.

Chronic, incidental exposures to radicals can cause skin and hair damage and lead to premature aging and the development of wrinkles.

There are no known products that implement a natural nutrient system, comprising lower nutrient levels of relevant ingredients administered through multiple and simultaneous delivery route methods to protect and promote the health and restoration of wounds to the hair, skin, nails and body.

There are no known products or methods to promote the cosmetic health and restoration of wrinkles to the skin, implementing natural, topical, enteral and injection methods for targeted results.

There are no known products or methods to promote the cosmetic health and restoration of hair and skin damage caused by a broad scope of burns and radiation exposures, such as the incidental radiation exposures from cell phones and computers.

There are no known products or methods to promote general health maintenance and management of nutrient levels, implementing natural, topical, enteral and injection methods to avoid nutrient level overload.

The invention fulfills such needs within the nutritional, cosmetic and healthcare industry, in particularly, addresses a need associated with major burn therapy and more practically, addresses an unfulfilled need associated with an expeditiously expanding industry of wireless technology and the adverse health effects thereof.

The system and methods will become apparent hereinafter.

SUMMARY OF THE INVENTION

Scientific studies and years of trial and error within the fields of nutrition science and the emerging field of nutritional cosmetic science have proven the benefits gained from optimizing nutrient performance. Despite the ongoing risks of overload and toxicity caused by mismanaged high potency nutrient dispensation, therapeutic benefits observed from nutrient potentization demonstrate worthy of pursuance, in particularly, if the risks of nutrient level overload and toxicity can be effectively managed.

The invention overcomes the limiting results and potentially unsafe effects of preparations comprising synthetic ingredients, high nutrient/volume level systems and the tedious regime of ingesting high volumes of food based nutrients, as well as the end user fears of body weight gain and nutrient overload.

The invention is based on the inventor's findings of an unexpected and unreported synergistic potentiation between a low nutrient level composition of a lipid based nutrient system, comprising nutritives, such as phosphorus, administered simultaneously through multiple routes of administration.

The nutrient system of the invention implements low level, non toxic substances that have reproducibly proven to regenerate the tissues and cells of the body; food sourced extracts. Such proven substance demonstrates permanent therapeutic and cosmetic results when strategically potentiated and administered simultaneously through multiple delivery routes. Inventor has discovered that the system of the present invention is a safely managed, potentized therapeutic form.

Attempts at optimizing nutrient performance, implementing high nutrient level dispensation is practiced to elevate the intracellular levels of the nutrients to rapidly initiate metabolic function to derive therapeutic benefits therefrom. Mismanaged individual route dispensation, implementing high nutrient levels, has proven to induce nutrient overload and toxicity effects. High nutrient levels when dispensed simultaneously through multiple routes would likely lead to nutrient overload.

As a departure from higher nutrient level/volume dose potentization practices, by introducing a low level, yet energetically potentiated nutrient form to a biological organism as a simultaneous ingestible, topical and injectable application, a safer and more efficient therapeutic dynamic is achieved. This methodology activates potentized metabolism for accelerated cellular regeneration and without adverse side effects, such as nutrient overload.

Through the implementation of the multiple routes of administration, in co-action with the lower nutrient levels of the bioactive ingredient components, a dynamic process is rendered, thereby, providing a system and methods for a safe, efficient and reproducible therapeutic potentization to provide exceptional aesthetic enhancements of the hair, skin and nails, while managing the risks of potential nutrient level overdose.

Furthermore, inventor has discovered that when implemented accordingly, the non-toxic ingredients and nutrient levels of the present invention may be subtlety potentized to induce enhancements of the hair, skin and nails, accommodating animals, humans of all ages, including infants and children. The system and methods of the invention may also be implemented safely for long term use and without inducing adverse effects or organism injury.

An embodiment of the nutrient system of the invention implements a "single formula" dispensation technique, whereby, the same, single formula of the nutrient system ingredients is dispensed simultaneously through multiple delivery routes.

The single formula of the nutrient system is administered in simultaneous doses at low nutrient levels through multiple delivery routes for efficient bioenergetic activation. This process induces a dynamic therapeutic potentization to achieve rapid metabolism of the nutrient system.

As an embodiment, the invention implements a targeted simultaneous injection, a topical application and an enteral administration method of said nutrient composition. The nutrient system may also be administered in successive dose repetitions to achieve progressive enhancement results.

Mismanaged methods to thoroughly disperse and potentize, implementing elevated nutrient levels and volume level doses administered simultaneously and successively through multiple routes would likely lead to nutrient level overload. The goal of the invention is to solve this problem by simultaneously supplying the targeted area with a potentiated low level nutrient system topically applied, while introducing the low level nutrient system enterally and into the tissues as an injection. The system and methods will provide efficient nutrient dispersion, diffusion and absorption to rapidly activate the bioenergetic systems, yet, not induce nutrient overload.

As an additional embodiment, the low level nutrient system may be simultaneously injected and applied topically to targeted areas of the body. The nutrient system may also be ingested and applied topically to targeted areas of the body for therapeutic and cosmetic enhancement.

As a therapeutic modality, such as a nutritional supplement routine is prescribed by a physician to be ingested daily as a dietary supplement for the purpose of progressive therapeutic benefits to overall health, the nutritional cosmetic system of the invention induces this inherent action for therapeutic and cosmetic enhancements.

As a further additional embodiment for general nutritional therapeutic maintenance of overall health, the nutrient system of the invention may be orally administered daily, simultaneously with a topical/transdermal application to a portion of the body. As a variation of the aforementioned embodiment and as a specific nutritional therapeutic, the nutrient system may comprise a prescribed nutrient and may be intravenously injected and topically applied.

The invention may implement phosphorus in various forms to potentiate the nutrient system action.

Delivery of the low level phosphorous potentiated nutrient system dilution of the invention, through the simultaneous multiple routes of administration will "bio energetically potentize" said nutrient system. The nutrient system of the invention may be further potentiated through carefully prescribed and managed successive dose repetitions. The human or animal organism will inherently potentize said nutrient system through the dynamic bioenergetic systems, without nutrient overload.

The invention proposes that a nutrient system potentiated by phosphorus (P) and phospholipids will induce effective bio energetic activity and progressive cellular regeneration. Therewithal, simultaneous and successive administration of a potentiated low level phosphorous-enriched nutrient form enhances these effects as a bioenergetic booster.

As an embodiment, the invention implements flax oil as a component. Flax oil has demonstrated exceptional health and cosmetic enhancing performance of the hair, skin and nails. An embodiment of the nutrient system comprises a lipid system of food based extracts and nutrients, such as flax oil, vitamin C, vitamin E and minerals, such as trace minerals. The said nutrient system may comprise B vitamins and minerals or any added nutrient substance to enhance energy metabolism.

The nutrient system of the invention will effectively fortify and reconstruct the lipids of the hair, skin, tissues and fingernail plates.

An embodiment of the invention may include modified nutrient system form, such as a material substance dilution.

As an embodiment of the invention, the nutrient system may be formulated as a low nutrient level dilution for the injectable, topical administration and for the enteral administration.

In accordance with inventor's further experimentations, personally formulating and utilizing hand made material substance dilutions and sub molecular homeopathic dilutions for personal and private use, inventor has developed an additional complementary nutrient form.

An embodiment of the invention may implement natural, non toxic food based substance and added nutritives, potentized by the classic homeopathic serial dilution and succussion steps (Hahnemann) and may be implemented as a complementary application with the material substance form of the nutrient system for therapeutic or cosmetic enhancements.

As a departure from the classical homeopathic substance dilution, the invention implements a natural and food based extract nutrient system for therapeutic and cosmetic enhancement.

When implemented accordingly, the nontoxic formula and nutrient levels of the invention may be safely and subtly potentized through the classic homeopathic process and without inducing adverse effects, as a complimentary nutrient system form.

The background fails to disclose a nutritional and cosmetic product and system of natural compositions, comprising lipids and minerals, such as phosphorus as its principle ingredients within a single formula nutrient system, delivered simultaneously as a method for topical, ingestible and injectable applications and as an efficiently potentized product and system to promote the health, growth and repair of the hair, skin, nails and body.

An embodiment of the system and methods of the invention may be implemented as a safer therapeutic for intestinal health. Nutritives, such as phosphorus (Manz 1992) and coconut oil (Fletcher) provide natural anti fungal, probiotic action. As an embodiment for improved intestinal health, the nutrient system of the invention comprising relevant nutritive compounds, such as phosphorus and coconut oil, may be simultaneously applied topically to the abdomen, while orally ingesting the nutrient system. An injection may also be administered implementing the gentle, low concentration formula of the invention. The nourishing biocompatible and relevant nutrient system will safely promote intestinal health by introducing a low nutrient level and volume level formula and without inducing nutrient overload imbalances or irritation and injury to delicate intestinal flora, due to potentially toxic synthetic ingredients.

An additional embodiment of the invention implements a natural nutrient system of relevant ingredients and multiple delivery route methods to protect and promote the health and restoration of hair, skin and nails, such as burns from all types of heat and radiation exposures.

The phosphorus enriched product and system of the invention is a safe and effective, non-operative, yet primary therapeutic method to skin burn and scar therapy and the treatment of hypophosphatemia. The product and system of the invention will replenish depleted phosphorus levels of the body, which is a requisite component for effective cellular regeneration and will assist to eliminate potential transcellular shifts in phosphorus due to major burn wounds and tissue trauma.

Oxygen radicals can be augmented or reduced by environmental, nutritional or hormonal influences. (Marnett).

Antioxidants, such as vitamin C and E have demonstrated protective effects against potential damage from radiation exposure. (Okunieff et al.)

As an additional embodiment, the invention implements a nutritional lipid and antioxidant comprised product, system and simultaneously administered method to protect biological tissues and restore radiation damaged tissues. The nourishing linoleic acid and antioxidant enriched nutrient system of the invention will protect and replenish hair, skin and nails from cell damage and from all types of burns, such as from UV from the sun, radiation sources, such as cell phones and computers, and from radiation therapies implemented for conditions, such as cancer.

The nutrient system of the invention may be delivered to the targeted area of the skin or surrounding tissues as a cell regenerative therapeutic to heal skin wounds and wrinkles.

The invention offers compositions and methods for permanent therapeutic wrinkle reduction and overall healthier facial, body skin and tissues. The EFAs and phospholipid enriched formula promote the effective release and activity of vital nerve transmitter impulses, which is crucial for muscle control, efficient blood flow and anti-inflammatory action required for inherent healing and restoration of skin ailments, such as wrinkles.

The simultaneous administration of the relevantly potentiated compositions and methods of the invention progressively perform to activate therapeutic, bioactivity of the target cells of the wound and wrinkle sites to permanently enhance the aesthetic appearance of such skin wounds and wrinkles and without inducing adverse effects.

In light of the foregoing, it is an advantage of the invention to provide a simultaneous ingestible, topical and injectable nutritional cosmetic product and delivery method system for improving the health, growth, appearance, texture of the hair, skin and nails, while managing risks of potential nutrient level toxicity and overload.

An additional advantage of the invention implements a strategically modified composition of lower nutrient levels, according to a minimum effective dose concept, thereby, modifying the nutrient system to render the composition as a highly bioavailable and bioactive form.

Another advantage of the invention is to implement phosphorus potentiated, non toxic substances that have reproducibly proven to regenerate the tissues and cells of the body; food sourced extracts.

A further advantage of the invention provides a naturally cultivated nutrient system implemented for permanent aesthetic enhancements as an alternative to toxic preparations for targeted injections systems limited to temporary enhancements.

Another advantage of the invention is to provide a system for permanent facial firming enhancements, such as wrinkle and lip enhancements, requiring no surgery.

A further advantage of the invention is to provide a natural and therapeutic product and system, which induces accelerated hair growth and permanently enhanced color tones to grey or aging hair without potentially toxic synthetic ingredients.

An additional further advantage of the invention provides an injectable, ingestible and topical (and transdermal) application of the nutrient system, such as for skin wound, scar or burn wounds as a safer alternative and non-operative, yet primary burn therapy technique.

A yet further advantage of the invention is to offer a therapeutic nutrient system comprising lipids, antioxidants and other relevant nutritives to implement for therapeutic restoration of tissue damage from all sources of radiation exposures.

Lastly, an advantage of the invention provides a dynamic system of integral nutrient and method components that when implemented simultaneously, co-act in a synergistic mode, rendering a safe, efficient therapeutic "bioenergetic potentization", which produces progressive aesthetic enhancements of the hair, skin and nails.

In light of these and other advantages, the invention provides a nutritional and cosmetic system and product for promoting the health, growth, repair, visual appearance and texture of hair, skin, tissues, nails and body.

The invention is potentized by the unique synergistic interactions of the interdependent, low nutrient level composition, by the addition of the phosphorus formula as a catalyst and by the dynamic, physiological interactions induced by the integration of the nutrient system and simultaneous and multiple delivery routes. The nutrient system and delivery methods may be strategically customized to skillfully execute safe potency management. The invention produces dynamic affects induced from the integral components of the system. The enhancement effects are accelerated in progressive stages of therapeutic regeneration, followed by enhanced and refined texture and color characteristics of the hair, skin and nails.

When implemented accordingly, the non-toxic formula and nutrient levels of the invention may be safely managed and utilized daily and consistently on animals and humans of all ages, including infants, children and sensitized individuals.

The nourishing nutrient system will maintain and improve the overall health of the organism, while restoring aesthetic characteristics and without inducing adverse effects.

The invention will now be described with particular reference to the accompanying drawings. Although particular embodiments of the invention may be disclosed, various modifications may be made without departing from the scope of the invention.

BRIEF DESCRIPTION OF TIM DRAWINGS

FIG. 1. is an introduction to the nutritional cosmetic system of the instant invention.

FIG. 2. is an introduction statement to the nutritional cosmetic system overview of the instant invention.

FIG. 3 is a description of the nutrient system formulation with examples in accordance with the instant invention.

FIG. 4 is a description of the phosphorous nutrient system formulation in accordance with the instant invention.

FIG. 5 is a description of the delivery methods of the nutrient system formulation in accordance with the instant invention.

FIG. 6 is a description of the therapeutic action of the nutrient system formulation in accordance with the instant invention.

FIG. 7 is a description of the therapeutic results rendered by the nutrient system formulation in accordance with the instant invention.

FIG. 8 is a copyright notice for the description of the nutrient system formulations and methods of delivery of the instant invention.

DETAILED DESCRIPTION OF THE INVENTION

The Nutrient System

The nutrient system embodiments of the invention are generally referenced as an ingestible, topical and injectable nutritional, therapeutic and cosmetic, nutritive, nutrient, extract, oil, liquid, formula, "single formula", nutrient system (NS), nutrient system dilution (NS dilution), emulsion, substance, material substance, material substance dilution, lipid system, preparation, product, derivative, system and, or method, applied to the hair, skin and nails or to any part of the body, or injecting into any part of the body, for maintaining general health, or for promoting growth and regeneration of the affected areas of the body, or for any therapeutic or cosmetic condition of human, animal or living organisms.

Examples of the Nutrient System Components

A blend of food based extracts, including lipid extracts and nutritives, such as:
Aloe;
Olive;
Corn;
Almond;
Safflower;
Spinach;
Kelp;
Rice;
Coconut; and
Seed extracts, such as;
Flax;
Passion fruit;
pumpkin;
Borage;
Carrot;
Broccoli;
Raspberry;
Kalahari;
Apple; and
Avocado,
Nutritives, such as plant sourced silica;
Oat Straw;
Horsetail; and
Aromatic extracts, such as;
Vanilla oil;
Coconut oil;
Rosemary oil; and
Vitamins, herbs and seed extracts as preservatives:
Vitamin C;
Vitamin E;
Grape seed oil;
Citrus seed oil;
Rosemary oil;
Thyme oil; and
Antioxidants, such as;
Vitamin E;
Vitamin C; and
A blend of vitamins, such as
Vitamin C; and
Minerals, such as;
Silica; and
A phosphorus blend formula;
Phosphorus (P); and
Supplemental sources of phospholipids;
Phosphatidyl choline;
Phosphatidyl serine;
Phosphatidyl ethanolamine; and
Phosphatidyl
A blend of nutrients for phosphorus metabolism;
Vitamin B8;
Vitamin B6;
Calcium;
Magnesium;
Vitamin D.

The nutrient system is frequently referenced as a dilution to denote the low level nutrient fluid form, however, it may be formulated in additional embodiment mediums which will become apparent hereinafter.

The nutrient system formula comprises a variety of natural food sourced ingredients. As examples, an embodiment comprising pure, organic olive oil and other nutritive ingredients may be ingested, while topically applying and massaging the olive oil preparation onto the hair, skin and nails to moisturize and promote strength and resilience. As an additional embodiment, a topical and ingestible corn and coconut oil nutrient system preparation can also be simultaneously ingested and topically applied as a protective skin conditioner and tanning oil prior to being exposed to the sun.

The invention may comprise flax oil, vitamin C and minerals such as phosphorus as a relevant ingredients of an embodiment. According to experiments performed by the inventor, flax oil has demonstrated to be an exceptional seed oil for use in preparations for the hair, skin, and nails, producing characteristic enhancements such as a remarkable strength, sheen and growth of hair and nails and a softer, smoother texture to skin, as well as progressively developed color tone effects to the hair.

The hair, skin and nails system and products principle active ingredients comprise food sourced extracts such as lipids, vitamins, such as vitamin C and biotin and minerals such as calcium, phosphorus and silica, which are relevant to the health and enhancement of the hair, skin and nails and to the principle therapeutic action of the formula. The lipid extracts, vitamin, mineral and other nutritive ingredients that are utilized by the system, comprise bio-affecting agents and compounds that have performed optimally and have demonstrated in repeated experiments by the inventor to nourish the health and enhancement of the hair, skin and nails.

Minerals such as silica may be sourced from herbs known to be high in this mineral, such as horsetail or oat straw. The formula may be preserved utilizing natural anti-oxidants, such as vitamin C, vitamin E and citrus seed or grape seed extracts. Other natural preservatives may be implemented, such as extracts that have a concentrated anti-oxidant effect, such as oils of thyme or rosemary extract.

The nutrient system may be deliberately formulated to achieve a higher level of bioactivity, bioavailability and biocompatibility of the inherent nutritive compounds.

The nutrient system form may comprise nutrient levels equivalent to or less than levels found in naturally occurring foodstuffs. Foodstuffs may include any food or plant origin for human consumption.

The invention provides a natural and health promoting cosmetic product and methods of use that may embody this formula, wherein all food sourced ingredients may be naturally derived, organic, raw and, or whole sourced.

The invention may be derived through cold pressed or a natural extraction methods where possible to preserve optimal bioactivity of the nutrient system. The invention may implement natural solvent methods to effectively cultivate the phospholipid content.

The invention may cultivate and implement methods to retain the inherent nature of the natural nutrient substances and form. Example 1; the extraction process may derive a virgin form. Example 2; the extraction process may derive an expeller pressed, cold pressed form or a natural extraction form. Example 3; the processes may resource organic, raw and whole plant extracts, without genetic modifications to preserve the inherent nature of the bioactive compounds of the foodstuff extracts, thus, resulting in an exemplary form; Organically produced plant sources contribute to the pure essence of the formula which is conducive to the efficient absorption of the nutrient components to promote optimal metabolic potentization. Example 4; the formula may also be preserved implementing temperature control methods, such as refrigeration.

The invention may cultivate the raw components of the extracts, sourcing the whole plant where possible; seed extracts, skin extracts and pulp extracts, as examples to retain a concentrated form of various inherent and complementary bioactives of the plant.

The invention also implements nutrient components relevant to the hair, skin and nails for multi actions. Example 1; vitamin C and vitamin E have demonstrated to be natural and effective antioxidant preservatives and necessary nutrients for the therapeutic regeneration of the hair; skin and nails and for protection from UV rays and additional radiation exposures, such as proximal exposures from cell phones, computers and radiation therapy. Example 2; Coconut oil consists of relevant bioactive such as fatty acids which nourish the health and enhancement of the hair, skin and nails. In addition, coconut oil is an effective anti fungal. Coconut oil may also contribute to the natural and subtle aroma of the formula. Example 3; Broccoli seed oil consists of nutrients such as significant levels of calcium and magnesium which represent food sourced, interdependent nutrients necessary for metabolism within the formula. Broccoli seed oil also consists of nutrients such as sulphur compounds and phytonutrients, which are relevant nutrients for the health and enhancement of the hair, skin and nails. Example 4; the mineral phosphorus serves as a nutrient catalyst within the formula, as an essential nutrient to regenerate the hair, skin and nails and also as an effective therapeutic nutrient for the regeneration of tissue damage due to radiation exposures and in the initial and recovery phases of major burn therapy.

The nutrient system is primarily comprised of food sourced nutritive ingredients, implementing the natural and inherent, lower nutrient levels and nutrient synergy of the plant extracts, sourcing a variety of plant based food groups, supplemented with additional nutrients. Alternative sources of plant food groups may be utilized. Alternative sources of lipids, other than plant based may also be utilized.

The nutrient formula of the invention utilizes the naturally occurring, lower level food sourced nutrients and compounds, such as macronutrients, micronutrients, phytonutrients, antioxidants and lipids end the naturally occurring nutrients yet discovered, supplementing the formula with lower nutrient levels of vitamins, minerals, and various nutrients and their interdependent nutrients, which are principle to the formula's action. The nutrient system may comprise nutritives for energy metabolism, such as 13 vitamins; thiamin, riboflavin, niacin, 136, B12, folate, pantothentic acid, biotin, choline and minerals, such as iodine, chromium, manganese and sulfur or any nutritive to assist in energy metabolism, such as amino acids.

Although plant based, food sourced extracts comprise a composition, of inherent nutrients, a blended form of food sourced extracts supplemented with interdependent nutrients, demonstrate more efficient synergistic potentiation.

The nutritive elements of the invention may be formulated to replicate the inherent nature and nutrient levels of natural food based chemistry and composition. One dose of the nutrient system may comprise the approximate nutrient levels equivalent to, or the nutrient levels lower than an adequate serving portion from the combined plant based food groups. Daily dosage of the nutrient system may comprise the nutrient levels from adequate serving portions of the various plant based food groups. The invention may also be formulated to comprise a minimum effective, physiological dose level, thereby, the nutrient components may be present in lower levels, sufficient to produce biological action. The nutrient system ingredients of the present invention may be standardized for quality control and to promote reproducible therapeutic effects.

The inherent nature of the nutrient system composition and the lower level nutritive form is conducive to an efficient level of biocompatibility and bioactivity of the nutrient system.

The material substance dilution form of the invention is further conducive to a higher level of biocompatibility and bioactivity of the nutrient system.

The presence of phosphorus (P) and phospholipids within the nutrient system produce potentiation of the inherent low level nutrient system form.

Simultaneous dispensation through multiple delivery routes of administration, induces an efficient level of bioactivity and bioavailability of the inherent, lower level, phosphorus potentiated nutrient system form.

In coaction with the application techniques, the highly biocompatible and bioactive lower level nutrient form induces synergistic interactions, activating dynamic therapeutic potentization.

The Nutrient System Applications

The nutrient system of the invention may encompass a variety of applications.

In accordance with the invention for general enhancements and daily use by the end user, the nutritional and cosmetic product and system may be applied to the hair directly or in a shampoo, to the face, nails or any portion of the body; In reference to hair, the product containing the formula may be used as a pre-style treatment for hair prior to blow drying or styling to help protect hair from the heat damage due to styling tools. The product containing the formula may also be mixed with shampoo or used as a pre-treatment conditioner for hair prior to shampooing to prevent damage and dehydration from harsh detergents and to lightly scent the hair of coconut and vanilla, in reference to skin, the preparation may be applied to the face to promote a softer, smoother texture, even skin tone and reduction of lines, scars and blemishes. In reference to the nails, the preparation may be applied to the fingernails to promote strength, resilience and growth. The formula may also be applied to any skin area on the body and used as a massage oil. As a topical application, a nightly application prior to sleep is conducive to effective results. The nourishing nutrient formula may also be implemented as a bath water infusion. Because of the inherently pure and lower level nutrient ingredients, the product of the invention is safe for use as a daily moisturizer on the skin, scalp and around eyes, for use on animals, humans of all ages, including infants and children, for all skin types and individuals who are skin sensitive. The formula may be used to help protect hair, skin and nails from the heat and UV rays from the sun and is therefore an effective nutrient system for UV protection. The nourishing nutrient formula of the invention protects and repairs skin and tissues from potentially harmful radiation sources.

For potent results, an ingestible application may be administered simultaneously with the aforementioned topical applications. To efficiently potentize the nutrient system for accelerated effects, an injectable application may be simultaneously administered with the topical and injectable applications, according to a professional practitioner's delivery system prescription (FIG. 2). The applications may be continuously and successively implemented daily to produce progressive, aesthetic enhancements.

The product of the invention may be implemented to promote specific enhancements; The product may be utilized for therapeutic regeneration and restoration of damaged skin due to wounds, burns or scars or blemishes. For specific firming enhancements to the facial skin, the formula may be ingested and topically applied to the facial skin and also to the scalp area around the face. The formula may also be applied underneath the chin area and down the neck to promote effective, firming enhancements of the face, neck and chin. The product of the invention may also be utilized on hair, eye brows and eyelashes to gently promote the health, growth, length and sheen, while enhancing the natural color tones to diminishing color, such as in greying hair. To promote the growth and natural color tones of the eyelashes, the formula may be topically applied to the base of the eyelashes, while dually ingesting the formula. The formula may also be simultaneously ingested and applied to the eyebrows to promote growth and color enhancement effects. The method of the application techniques may be modified; the technique to promote enhancements of the eye brows may be modified to inject the formula into the eyebrow area. Successive applications of the formula of the invention will demonstrate progressive enhancements, such as refined skin texture and deeper, richer color tones to the hair, eyelashes and eyebrows and a visual sheen to the hair, skin and nails. When used accordingly, the nutritional and cosmetic product and system improves the health, growth, appearance and texture of the hair, skin and nails.

The Nutrient System Formulations and Mediums

The invention may comprise a variety of formulations and mediums.

The invention may comprise a lipid system of naturally occurring compounds or oils, such as fatty acids, comprising added nutritives.

The nutrient, system may comprise variant formulas and mediums such as a dilution, emulsion, infusion, solution, colloid, suspension and material substance form, as a cream, compress, lotion, pill, tablet, pellet, liquid, oil, powder and in any form or medium that contains the nutrient system.

The invention may be formulated as a material substance form, comprising material substance of food sourced extracts (NS). The invention may be formulated as a dilution, such as simple dilution, doubling dilution or serial dilution, comprising the material substance of food sourced extracts (NS dilution). The invention may be formulated as a material substance dilution form, comprising trace elements of plant hydrophyllic or sea water derived elements, with a liquid mineral dilution, colloid minerals form or with any modified water form, such as H2 enriched, ph modified water or molecularly restructured water or dilutions. The invention may comprise a formulation mixture of the material substance form and a tissue or cell salts dilution.

The nutrient system formula may be formulated for end user or professional practitioner applications. The ingestible product of the invention may comprise a liquid that may be encapsulated or placed in a bottle so as to be contained in its pure liquid extract form, and may comprise a (single formula) 2 bottle variation form, including 1 bottle for the ingestible application and 1 bottle for the topical application, or dry ingredient ingestible forms such as cellulose capsules or tablets+liquid topical form. A variation may include a dry form to be mixed with water or liquid to ingest and to apply topically. The nutrient system of the invention may be formulated as a biocompatible liquid form (such as an emulsion or solution) contained within ampoules or vials for professional applications, such as injection and intravenous use. The invention may also comprise a separate form for eyelashes and eyebrows to simultaneously apply topically and to ingest. The invention may include a variation for cosmetic injection purposes to be injected into the dermis, while simultaneously ingesting the formula. As intravenous applications of nutritives are utilized for therapeutic purpose; a simultaneous intravenous and topical application of the formula may be implemented for cosmetic purposes. As a liquid, emulsion or dilution, the invention may be formulated as a biocompatible form of lipid intravenous administration. The nutrient system forms may comprise the derivatives of food nutrients and may be comprised as a safe form for intravenous, injectable or enteral administration. When administering the enteral applications, a sublingually dispensed application may be administered. Enteral, topical and transdermal applications may also be implemented simultaneously with various injection routes, such as the ocular, nasal, inhalation and ear canal routes, cutaneous and subcutaneous injection routes; microportation, intradermal injection, transdermal, intramuscular injection, or injection into an organ, intraarterial injection, enemata, vaginal and rectal, implantation and suppositories, sprays and drop forms, or any wound based delivery route.

The Customized Nutrient System Formulations

Customized variation of the nutrient components of the formula should be evaluated such as for an individual who is sensitized to a requisite ingredient component.

Example 1; individuals who are diagnosed to be sensitized to an ingredient component of the nutrient system formula and who require burn therapy; a customized formulation may be prescribed as to substitute the sensitized component for an equivalent phospholipid ingredient component, which is a necessary component for the performance and the action of the formula and is also an essential nutritive component for burn therapy. In addition to the necessary health benefits, sensitivity elimination renders a higher level of biocompatibility and bioactivity of the nutrient system. Sensitivity evaluation should be conducted, prior to administration of the formula ingredients. Example 2; As an embodiment for specific, therapeutic application, a customized iron comprising formulation may be prescribed for individuals who are diagnosed with a iron deficiency. (FIG. 2 designated application 16B)

The Phosphorus Nutrient System

An embodiment of the invention includes a proprietary phosphorus nutrient system. The phosphorus formula performs essential therapeutic action.

The phosphorus formula comprises a blend of the mineral phosphorus (P), natural lipids from food based sources and supplemental sources of phospholipids which may include one or more of the following; phosphatidyl choline, phosphatidyl serine, phosphatidyl ethanol amine and phosphatidyl inositol. The phosphorus formula of the invention may comprise a lipid system of naturally occurring fatty acids bound in a phospholipid structure. The phosphorus nutrient system may comprise interdependent nutrients involved in phosphorus metabolism, such as phosphorus (P), vitamin BS, vitamin B6, calcium, magnesium, vitamin and chloride.

Food based sources of these interdependent nutrients should also be included where possible. Food based components within the nutrient system may already contain phosphorus EFAs in an amount and form, to which a phosphorus nutrient system blend is combined to potentiate the inherent nutrient form.

Although the proprietary phosphorus nutrient system comprises a blend of the relevant mineral, the phosphorus nutrient system may comprise nutrient levels as a slightly concentrated, lower level form.

Phosphorus sources and seed extracts provide a synergistic collaboration. The formula of the invention may comprise seed extracts, which comprise higher levels of phosphorus and naturally occurring compounds, such as antioxidants. As discovered by the inventor, in coaction with the phosphorus nutrient system, the bioactive compounds inherent to the seed oil extracts induce potentiated action of the formula, resulting in accelerative regeneration of the hair, skin and nails. The formula may comprise components to assist in metabolism of the seed extracts, such as a natural enzyme.

As an integral component to the formula of the invention, the phosphorus blend is present to catalyze a synergistic nutrient system and delivery route collaboration to achieve an efficient therapeutic potentization.

As discovered by the inventor, the active agents inherent to the phosphorus formula perform as catalysts and nutrient potentiators, interacting with the bioactive ingredient components of the principle nutrient system formula, inducing an efficient level of intracellular absorption of the nutrient components and activating potentization. Furthermore, the synergistic interactions will induce accelerative therapeutic action of the nutrient system when delivered through simultaneous multiple routes of administration, resulting in rapid cellular regeneration.

The presence of the mineral phosphorus within the formula of the invention performs an additional specific, therapeutic purpose.

The formulas and methods of the invention may be implemented to treat injured or damaged skin or tissues, such as wrinkles, wounds, scars and burns to the skin or deeper structures, (generally "wound"). The product and system of the invention is a safe and effective, non-operative, yet primary therapeutic method to skin burn and scar therapy and the treatment of hypophosphatemia (decreased plasma and/or intracellular phosphate concentration). Depletion of phosphate levels has been observed to occur in major urn wound patients. (The Merck Manual). Phosphate administration is prescribed when depletion is diagnosed. The invention is an effective and safely managed phosphorus repletion protocol when phosphorus replacement and redistribution is indicated. The product and system of the invention will replenish depleted phosphorus levels of the body, which is a requisite component for effective cellular regeneration and will assist to eliminate potential transcellular shifts in phosphorus due to major burn wounds and tissue trauma. A strategically prescribed regimen of simultaneous topical, enteral, cutaneous and intravenous injections of the nutrient system provides a rapid-acting and precisely targeted delivery system and eliminates the potential risks of conventional phosphorus repletion protocols, such as nutrient level overdosing from mismanaged individual route administration. (FIG. 1; example 11, B).

The invention may also be safely utilized where the parenteral route of administration is prescribed. A dilution of the nutrient system of the invention (NS dilution) may be implemented for effective burn and hypophosphatemia therapies, as a safely tolerated intravenous method of administration. As an embodiment for intravenous application, the nutrient system may comprise the minerals relevant to burn therapies, such as tissue salts of phosphorous, silica, sodium and potassium.

The invention is also an effective treatment for major burns, whereby, direct topical contact of the burn or wound site is contraindicated. A micro emulsion in a spray form of the nutrient system dilution may be implemented and is safe and effective for a non direct topical contact application of the burn wound.

The nourishing nutrient formula may be applied externally onto the skin of the wound in a mist or spray form, or any form implemented for a non direct topical application, while simultaneously injecting and ingesting the formula of the nutrient system. The formula may be implemented as a non direct topical application and/or injected into an application location surrounding the burn wound site, while simultaneously implementing the orally administered application of the nutrient system formula and is effective for ailments, such as for deep skin wounds. A subcutaneous and targeted injection of the nutrient system formula may be implemented to the deeper layers of the burn site and/or surrounding the wound site. A cutaneous injection may be implemented to the live tissues and structures surrounding the wound site. Multiple delivery route administration will activate the nourishing nutrients of the formula and induce the transdermal diffusion effect, resulting in efficient absorption of the nutrients to the surrounding tissues and into the targeted wound site to promote cellular regeneration and restoration and may also be implemented for major burns that affect the deeper structures of the body, such as the fat, muscle tissue, hone cartilage and joint tissues. The system of the invention will also promote restoration of tissue damage due to cell degeneration, such as scars to the skin that may occur following the initial recovery phases of burn wounds. As a method of followup care subsequent to critical care for major burn wounds, the successive applications of the formula's nourishing and relevant nutrients, will promote progressive enhancements of any skin blemishes, wounds or sears.

The Nutrient System Modifications

Modifications of the nutrient component levels and form may be prescribed, such as for purposes of potency management. An embodiment of the nutrient system of the invention may refer to a nutrient system that may be diluted, whereby, material substance remains; a dilution of the nutrient system (NS dilution).

The nutrient system primarily resources the natural and inherent, lower nutrient levels of the foodstuff extracts, which thereafter, are safely and efficiently potentized by the multiple routes of administration (application techniques). However, as an additional embodiment, the nutrient system form may be modified to comprise a homeopathic form.

As an additional complimentary embodiment, the invention may comprise a homeopathic succussed serial dilution form; diluted and succussed in series of repeated steps according to the strict process of a classic homeopathic serial dilution and whereby, material substance may not remain; the homeopathic form of the nutrient system; ("HOM"). The invention may comprise a proprietary potency and may not be implemented according to the strictest standards of the classical homeopathic assessment and prescription techniques.

The nutrient system of the invention may also be diluted and succussed to potentize according to homeopathic scales whereby material substance remains and may also be potentized as a sub molecular (non material substance) form. The sub molecular potency may be implemented for subcutaneous applications as prescribed for critical wounds to the deeper tissues of a major burn for hastened activation of the therapeutic nutrient system.

As further additional embodiments, the nutrient system of the invention may also be potentized for therapeutic restoration, whereby, a nutrient deficiency exists and may comprise an individually potentized nutrient such as phosphorus; The invention may comprise a formulation mixture of the material substance form, mixed with a homeopathically potentized nutrient, such as phosphorus, prescribed for a major burn patient who suffers from hypophosphatemia. The phosphorus nutrient system may also be homeopathically potentized for the major burn wound therapies.

The nutrient system may comprise a potentized nutrient such as iron, prescribed to a patient who suffers from iron deficiency anemia.

The Formulation Mixture

A mixture of the slightly concentrated, yet lower level nutrient system dilution form of the invention; (NS) and the homeopathic serial succussion and dilution form (HOM) may be combined as a formulation mixture and administered simultaneously.

The homeopathic dilution form (HOM), implemented as a complementary application with the nutrient system (NS) of the invention, is appropriate for single formula dispensation. Example 1; a formulation mixture of the nutrient system form (NS), comprising the homeopathic dilution (HOM), may be ingested and topically applied, while implementing an intravenous injection of the formulation mixture. Example 2; a formulation mixture of the nutrient system form (NS), comprising the homeopathic dilution (HOM), may be ingested and topically applied, while implementing an intravenous injection of the sub molecular homeopathic dilution form.

As an embodiment of the invention, the homeopathic form may be implemented as an initial therapeutic, in particularly, with the parenteral administrations whereby the enteral route is not implemented. (FIG. 2; designated application example 118). The homeopathic form may also be implemented for the more chronic conditions such as to the scars, wrinkles, wounds and to aging skin conditions. (FIG. 2; designated application example 7B).

As an embodiment of the invention, the complimentary application, comprising the homeopathic form may be implemented for acute conditions, such as the major burn therapies to further hasten activation of the nutrient system, as a temporary, rapid-acting therapeutic. Implementing the embodiment of homeopathic form as a long term therapeutic requires close monitoring by a professional. The nutrient system dilution form (NS dilution), administered through the multiple routes of administration, may be implemented for conditions, such as the major burn therapies, as a long term therapeutic. (NS dilution; not potentized through the homeopathic dilution and succussion process).

The Delivery Systems

The application techniques are implemented as delivery methods of dispensation and methods of potency activation and management, as prescribed according to the designated applications thereof. The invention provides a single formula of the nutrient system, implementing a dual-application delivery method application technique, which integrates an orally administered application with a topical and transdermal approach. The topical+ the injection applications of the nutrient system induce an accelerated transdermal diffusion effect. For efficient performance, the material substance form of the nutrient system (NS) may be implemented through the enteral route of administration, simultaneously with the topical and injectable routes. Subtle, physiological interactions are produced from the synergy of multiple delivery route dispensation. The multiple metabolic interactions induced from the bioactive nutrient components activate efficient potentization.

The successive dose regimen is a potency management technique.

Customized potency of the nutrient system is safely managed, evaluating the nutrient system forms, the delivery routes and the successive applications of a dose regimen, as prescribed according to designated applications; The nutrient system may be formulated to achieve customized potency. The application techniques may be skillfully executed to achieve a safely managed, customized potency of the nutrient system.

As an embodiment, implementing customized potency management; the topical and ingestible delivery methods will potentize the nutrient system dilution form of the invention for infants and children, (FIG. 2; designated application example 9).

The dilution form of the nutrient system may also be applied to a broad area of an infant's or child's body to induce a potentized transdermal effect. The aforementioned designated application may be implemented for animals of equivalent weight, however, the designated applications as prescribed for adults, may also be prescribed for larger animals, such as for animals requiring burn therapy treatment.

The Progressive Process of Therapeutic Action

The invention provides dynamic therapeutic processes in progressive stages. A regimen of successive doses will result in progressive aesthetic enhancements.

One dose of the nutrient system of the invention according to multiple routes of administration will achieve potentization, however, for the specific, therapeutic applications, such as for the burn therapies, the nutrient system may be administered more than once, according to a nutrient dose regimen of successive applications. (FIG. 2; designated application example 11).

Implementing a dose regimen of successive applications of the lower level nutrient system through multiple routes of administration, induces a higher level of bioactivity of the nutrient system, activating efficient potentization. Successive applications of the nutrient system, according to a dose regimen, will demonstrate progressive therapeutic and aesthetic enhancements.

Successive applications of the nutrient system will promote cellular regeneration, resulting in overall healthier skin and tissues. The implementation of the system of the present invention administered as a long term therapeutic will continue to promote further cellular regeneration and facial skin finning enhancements. Continuously activated through multiple mute delivery, the nutrient system's bin-affecting ingredients remain potentized and furthermore, will continue to promote progressive enhancements.

Successive applications of the nourishing nutrient system to the wound over a period of time will result in therapeutic regeneration and restoration of the wound, followed by the progressive aesthetic enhancement of the wound, which occur in progressive stages. This progressive dynamic action will also perform as indicated for specific therapeutic and cosmetic enhancements on the hair and nails and for all types of intrinsic and extrinsic anti-aging purposes. For example, to promote the growth and color tones of the eyebrows and eyelashes, the formula of the nutrient system may be topically applied to the brows and the base of the eyelids. To promote the finning enhancement of the face, the formula may be applied to the facial skin and also to the scalp area around the face and onto a wrinkle site. The formula may also be applied underneath the lower chin area and down the neck to promote effective and firming enhancements of the face and neck. For efficient potentization, an orally administered application of the nutrient system may be implemented simultaneously with the aforementioned applications.

The aforementioned steps should be repeated successively over a period of time to promote firming of the facial skin and progressively refined enhancements.

The nutrient system formula of the invention may be subcutaneously injected into the skin for accelerated cosmetic enhancements.

As an embodiment for accelerated skin and tissue firming enhancements of the facial skin such as for a wrinkle or scar, a simultaneous application of the nutrient system may be administered topically to the targeted site and subcutaneously injected into the skin of the targeted area of the wrinkle or scar site. The nutrient system will activate and potentize to promote cellular regeneration and therapeutic restoration of the skin of the wound affected area. An embodiment for targeted delivery and potentization of the nutrient system, implements the technique of injecting the potentiated nutrient system into the skin of the targeted area of the wrinkle site, while implementing the topical application technique onto the wrinkle or scar and simultaneously ingesting the formula. (FIG. 2; designated application example 1). To promote permanent cosmetic enhancement of the lips to achieve improved health and cellular regeneration for a fuller appearance, an simultaneous application of the nourishing nutrient system may be topically applied+an injection application into the lips+an orally administered application. The steps should be repeated long term for progressively refined, permanent results. (FIG. 2 designated application example 6).

The invention provides an additional embodiment for specific cosmetic enhancements, whereby, accelerated hair enhancement is desired, such as for the scalp and eyebrows. The orally administered application+topical application (the dual application delivery method)+the subcutaneous injection method technique should be implemented simultaneously to the targeted ailment affected site, such as to the scalp and eyebrows or any part of the body affected by hair loss or fading color, (FIG. 2; designated application example 5 A).

Subtle, physiological interactions are induced from the integration of the nutrient system and multiple route administration, implementing a single formula of low nutrient levels, simultaneously dispensed through multiple delivery routes of the organism will induce a uniformity of action effect. Thereby, as the synergistic bioactivity of the potentized nutrient system is maintained according to successive applications, the biological processes remain energetically optimized for therapeutic enhancement. The dynamically potentized targeted delivery system will result in progressive and precisely targeted, aesthetic enhancements and without causing nutrient overload.

The Designated Delivery Systems

Examples of the integration of the Nutrient System Forms, Application Techniques and Successive Nutrient Dose Regimens According to Designated Delivery Systems.

NS; The nutrient system; HOM; The homeopathic form of the nutrient system.

Dose repetitions according to a 12 hour interval of time are illustrated for example purposes. For rapid potency results, an orally administered dose of the NS should be implemented as an integral component to the delivery system designations. One dose of the nutrient system, according to multiple routes of administration will achieve potentiation, however, for the specific therapeutic applications, the nutrient system may be administered more than once, according to a nutrient dose regimen of successive applications.

Particular designated applications may be combined and administered simultaneously and in dose repetitions within a 24 hoer interval of time by end user; (Examples 3 and 16).

However, particular therapeutic applications should be implemented according to a professional practitioner's evaluation, prescription and administration, observing individual response (examples 1, 6, 9 and 12). Repetition of subsequent applications may be administered, observing individual response. Dose repetitions may be repeated more frequently (or more rapid successions) for conditions such as the acute and major burns wounds, according to practitioner observation. The injection applications may be followed up with daily oral and topical applications of the nutrient system by end user, as prescribed by practitioner. Potency management requirements and dose regimens may vary determined by the designated applications and according to weight, gender, life stage and health status.

Example 1

For Specific Targeted Enhancement of a Facial Wrinkle or Scar

An example of a successive dose regimen according to a designated application of a specific therapeutic enhancement to a deep wrinkle or sear for targeted aesthetic effects;

9 am a simultaneous subcutaneous injection of the formulation mixture of the NS dilution and the HOM dilution into the targeted area wrinkle/scar site+a topical application of the NS onto the targeted area wrinkle/scar site+an orally administered application of the formulation mixture of the NS dilution and the HOM dilution forms 12 pm a simultaneous topical application of the crude form of the NS onto the targeted area wrinkle/scar site+an orally administered application of the NS.

9 pm a simultaneous topical application of the NS onto the targeted area wrinkle/scar site+an orally administered application of the NS.

Example 2

For General Enhancements of Wrinkles to the Facial Skin 9 am

A simultaneous topical application of the NS onto the facial skin and wrinkle sites+an orally administered application of the NS.

9 pm

A simultaneous topical application of the NS onto the facial skin and wrinkle sites+an orally administered application of the N8.

Example 3

For Specific Targeted Enhancement of a Blemish or Scar to the Facial Skin 9 am A simultaneous topical application of the NS onto the targeted area blemish or scar site+an orally administered application of the NS.

12 pm a simultaneous topical application of the NS onto the targeted area blemish or scar site+an orally administered application of the NS.

9 pm a simultaneous topical application of the NS onto the targeted area blemish or scar site+an orally administered application of the NS.

Example 4

For Specific Targeted Enhancement to the Fingernails for Improved Growth, Strength, Resilience and Shine 9 am a simultaneous topical application of the NS onto the targeted area sites of the fingernail, finger nail bed and underneath the fingernail+an orally administered application of the NS.

9 pm a simultaneous topical application of the NS onto the targeted area sites of the fingernail, finger nail bed and underneath the fingernail+an orally administered application of the NS.

Example 5

For Specific Targeted Enhancement to the Hair, Eyebrows and Eyelashes for Enhanced Growth, Shine and Color Tones Designated Application A; 9 am a simultaneous subcutaneous injection of the NS dilution into the targeted area scalp, eyebrow and/or eyelash sites+a topical application of the NS onto the targeted area scalp, eyebrow and/or eyelash site+an orally administered application of the NS.

12 pm a simultaneous topical application of the NS onto the targeted area scalp, eyebrow and/or eyelash sites+an orally administered application of then NS of the nutrient system.

9 pm a simultaneous topical application of the NS onto the targeted area scalp, eyebrow and/or eyelash sites+an orally administered application of the NS of the nutrient system.

Designated Application B; 9 am a simultaneous subcutaneous injection of the formulation mixture of the NS dilution and HOM dilution form of the nutrient system into the targeted area scalp, eyebrow and/or eyelash sites+a topical application of the formulation mixture of the NS dilution and HOM dilution onto the targeted area scalp, eyebrow and/or eyelash site+an orally administered application of the NS.

12 pm a simultaneous topical application of the NS onto the targeted area scalp, eyebrow and/or eyelash sites+an orally administered application of the NS.

9 pm a simultaneous topical application of the NS onto the targeted area scalp, eyebrow and/or eyelash sites+an orally administered application of the NS.

Example 6

For Specific Targeted Enhancement to the Facial, Lips and Neck Skin for Firming and Anti-Aging Effects 9 am a simultaneous application of a subcutaneous injection of the formulation mixture of the NS dilution and the HOM dilution form into strategic points of the scalp, face, lips, chin and neck+a topical application of the NS onto the targeted area scalp, facial, chin and neck skin sites; the formula should be topically applied to the facial skin, lips and also to the scalp area around the face. The formula should also be applied underneath the lower chin area and down the neck+an orally administered application of the NS.

9 pm a simultaneous topical application of the NS onto the targeted area scalp, face, lips, chin and neck skin sites; the formula should be topically applied to the facial skin, lips and also to the scalp area around the face. The formula should also be applied underneath the lower chin area and down the neck+an orally administered application of the NS.

Example 7

For Specific Enhancement to the Facial Skin for Accelerated Firming of Aging Skin Designated Application A; 9 am a simultaneous topical application of the NS onto the targeted area scalp, facial, chin and neck skin sites; the formula should be topically applied to the facial skin and also to the scalp area around the face. The formula should also be applied underneath the lower chin area and down the neck+a subcutaneous injection of the NS dilution form to the targeted scalp, facial, chin and neck sites+an orally administered application of the NS.

12 pm a simultaneous topical application of the NS onto the targeted area scalp, facial, chin and neck skin sites; the formula should be topically applied to the facial skirt and also to the scalp area around the face. The formula should also be applied underneath the lower chin area and down the neck+an orally administered application of the NS.

Designated Application B; 9 am a simultaneous topical application of the formulation mixture of the NS dilution and the HOM dilution form of the nutrient system onto the targeted area scalp, facial, chin and neck skin sites; the formula should be topically applied to the facial skirt and also to the scalp area around the face. The formula should also be applied underneath the lower chin area and down the neck+a subcutaneous injection of the NS dilution to the targeted scalp, facial, chin and neck sites+an orally administered application of the formulation mixture of the MOM dilution form and the NS dilution.

12 pm a simultaneous topical application of the NS onto the targeted area scalp, facial, chin and neck skin sites; the formula should be topically applied to the facial skin and also to the scalp area around the face. The formula should also be applied underneath the lower chin area and down the neck+an orally administered application of the NS.

Example 8

For General Enhancement and Maintenance of Healthy Hair, Skin and Nails

For improved growth, softness and shine of hair, refined texture and radiant tone of the skin and improved growth, resilience and shine of the nails.

9 am

A simultaneous topical application of the NS onto the targeted area scalp hair, eyebrows, skin, fingernails and toenails sites an orally administered application of the NS.

9 pm

A simultaneous topical application of the NS onto the targeted area scalp hair, eyebrows, skin, fingernails and toenails sites+an orally administered application of the NS.

9 pm; Prior to Sleep a simultaneous topical application of the NS onto the targeted area scalp, facial, chin and neck skin sites; (the formula should be topically applied to the facial skin and also to the scalp area around the face. The formula should also be applied underneath the lower chin area and down the neck)+an orally administered application of the NS.

Example 9

A Specific Therapeutic for Irritant Diaper Dermatitis

An example of a successive dose regimen according to a designated application of a specific therapeutic application to the diaper area of an infant for relief of irritant diaper dermatitis (IDD);

8 pm; Prior to Sleep a simultaneous topical application of the dilution form of the nutrient system onto the targeted diaper area site+an orally administered application of the dilution form of the nutrient system.

Example 10

For General Enhancement to the Hair as a Pre-Treatment Fortification Prior to Shampooing and as Post Treatment after Shampooing An example of a successive dose regimen according to a designated application of a general cosmetic enhancement to the hair for health and hydration purposes. The formula may be mixed with shampoo prior to bathing, may be applied after shampooing, prior to utilization of styling tools. The nutrient system may also be applied to the skin and nails for pre treatment fortification.

9 am a simultaneous topical application of the NS onto the targeted area of the scalp hair, eyelash, eyebrow, skin and nail sites prior to bathing and shampooing+an orally administered application of the NS prior to bathing and shampooing.

9 pm; Prior to Sleep a simultaneous topical application of the NS onto the targeted area of the scalp hair, eyelash eyebrow, skin and nail sites post bathing and shampooing+an orally administered application of the NS post bathing and shampooing.

Example 11

For Specific Therapeutic Application to the Body for Major Burn Therapy

An example of a successive dose regimen according to a designated application of a specific therapeutic application to the body for a major burn affecting the deeper structures of the body, requiring critical care;

Designated Application A; 9 am

Simultaneous intravenous administration of the NS dilution+an orally administered application the NS+a subcutaneous and intramuscular injection of the NS dilution to the surrounding tissues, structures and deeper layers and structures of the targeted area burn site+a topical application of the NS dilution in a mist or spray form over, the targeted area burn site and the surrounding areas of the targeted area burn site.

12 pm a simultaneous topical application of the NS dilution in a mist or spray form over the targeted area burn site and the surrounding areas of the targeted area burn site+an orally administered application of the NS.

3 pm a simultaneous subcutaneous and intramuscular injection of the NS dilution to the surrounding tissues, structures and deeper layers and structures of the targeted area burn site+a topical application of the NS dilution in a mist or spray form over the targeted area burn site and the surrounding areas of the targeted area burn site+an orally administered application of the NS.

9 pm a simultaneous topical application of the NS dilution in a mist or spray form over the targeted area burn site and the surrounding areas of the targeted area burn site+an orally administered application of the NS.

Designated Application 13; 9 am

Simultaneous intravenous administration of the formulation mixture of the NS dilution and the HOM dilution of the nutrient system+a subcutaneous and intramuscular injection of the formulation mixture of the NS dilution and HOM dilution form to the surrounding tissues, structures and deeper layers and structures of the targeted area burn site+a topical application of the formulation mixture of the NS dilution and HOM dilution form in a mist or spray over the targeted area burn site and the surrounding areas of the targeted area burn site.

2 pm a simultaneous topical application of the NS dilution in a mist or spray form over the targeted area burn site and the surrounding areas of the targeted area burn site+is subcutaneous and intramuscular injection of the NS dilution.

3 pm a simultaneous subcutaneous and intramuscular injection of the NS dilution to the surrounding tissues, structures and deeper layers and structures of the targeted area burn site+a topical application of the NS dilution in a mist or spray form over the targeted area burn site and the surrounding areas of the targeted area burn site+an orally administered application of the NS.

9 pm a simultaneous topical application of the NS dilution in a mist or spray form over the targeted area burn site and the surrounding areas of the targeted area burn site+a subcutaneous and intramuscular injection of the NS dilution.

Examples 12

A Specific Therapeutic Massage Application to the Body for a Muscle Strain 11 am a simultaneous topical application of the NS onto the targeted area muscle strain site prior to massage+an orally administered application of the NS.

2 pm a simultaneous topical application of the NS onto the targeted area muscle strain site+an orally administered application of the NS.

9 pm a simultaneous topical application of the NS onto the targeted area muscle strain site+an orally administered application of the NS.

Example 13

A General Therapeutic Application for a Massage to the Body 10 am a simultaneous topical application of the NS onto the targeted massage areas of the body+an orally administered application of the NS, prior to massage.

10 pm; Prior to Sleep a simultaneous topical application of the NS onto the targeted massage areas of the body+an orally administered application of the NS.

Example 14

A General Therapeutic Enhancement to the Hair, Skin and Nails as a Pre-Treatment Fortification Prior to Sun and Radiation Exposure and as Post Treatment after Sun and Radiation Exposure An example of a successive dose regimen according to a designated application of a general therapeutic enhancement to the hair, skin and nails for UV protection and anti-aging purposes. The nutrient system formula may be applied in the morning and evening. The nutrient system may also be applied for protection and therapeutic restoration of radiation exposures and damage from daily cell phone, computer use and radiation therapies (radiation dermatitis).

11 am

A topical application of the NS to the hair, skin and nails prior to sun, cell phone and computer exposure; an orally administered application of the NS prior to sun, cell phone, computer use and radiation therapy.

9 pm; Prior to Sleep

A topical application of the crude form to the hair, skin and nails post sun, cell phone and computer exposure; an orally administered application of the crude form post sun, cell phone, computer exposure and radiation t Example 15

A Combined Designated Application

Example 4; for Specific Therapeutic and Cosmetic Enhancement to the Fingernails+Example 6; for Specific Therapeutic and Cosmetic Enhancement to the Facial Skin for Firming and Anti-Aging Effects An example of a successive dose regimen according to a designated application of a specific therapeutic and cosmetic enhancement to the facial skin and fingernails;

9 am a simultaneous topical application of the NS onto the targeted area scalp, facial, chin and neck skin site; (the formula should be topically applied to the facial skin and also to the scalp area around the face. The formula should also be applied underneath the lower chin area and down the neck) and to the targeted area sites of the fingernail, finger nail bad and underneath the fingernail+an orally administered application of the NS.

9 pm a simultaneous topical application of the NS onto the targeted area scalp, facial, chin and neck skin sites; (the formula should be topically applied to the facial skin and also to the scalp area around the face. The formula should also be applied underneath the lower chin area and down the neck) and to the targeted area sites of the fingernail, finger nail bed and underneath the fingernail+an orally administered application of the NS.

Example 16

For General Nutritional Maintenance of Overall Health

Designated Application A; 9 am an orally administered dose of the NS+a topical/transdermal dose of the NS to prescribed portion of the body.

9 pm an orally administered dose of the NS+a topical/transdermal dose of the NS to prescribed portion of the body.

Designated Application B

For Specific Maintenance of a Nutrient Deficiency 9 am an intravenously administered application of the NS dilution comprising a prescribed nutrient+a topical/transdermal dose of the NS comprising a prescribed nutrient to a predetermined portion of the body.

12 pm an orally administered dose of the NS comprising a prescribed nutrient+a topical/transdermal dose of the NS comprising a prescribed nutrient to a predetermined portion of the body.

9 pm an orally administered dose of the NS comprising a prescribed nutrient+a topical/transdermal dose of the NS comprising a prescribed nutrient to a predetermined portion of the body.

The invention has been shown and described herein in what is considered to be the most practical embodiment. It is recognized, however, that departures may be made therefrom within the scope of the invention and that obvious structural and/or functional modifications will occur to a person skilled in the art.

What is claimed is:

1. A method for improving the health and appearance of hair, skin and nails of a person or animal, comprising the steps of:
providing a nutrient system formula, said nutrient system formula including a nutrient system base formula having lipids, vitamin C, vitamin B7 and silica and a phosphorous nutrient system formula including phosphatidyl serine, phosphatidyl ethanolamine, vitamin B5, vitamin B6 and vitamin D;
ingesting said nutrient system formula by the person or the animal; and
injecting said nutrient system formula into the person or the animal.

2. A method as recited in claim 1, further comprising the step of:
topically applying said nutrient system formula on the person or the animal.

3. A method as recited in claim 1, wherein said formula further comprises:
flax oil.

4. A method as recited in claim 1, wherein said formula further comprises:
minerals.

5. A method as recited in claim 4, further comprising the step of:
topically applying said nutrient system formula on the person or the animal.

6. A method as recited in claim 1, further comprising the step of:
topically applying said formula to the hair, skin, nails or body, or wounds, scars, or burns for treatment or for regenerating muscles, bones, or joint tissue or for treating hypophosphatemia.

7. A method as recited in claim 1, further comprising the step of:
topically applying said nutrient system formula to the hair, skin, nails or body.

8. A method as recited in claim 7, wherein said steps of topically applying, injecting and ingesting said nutrient system formula are performed simultaneously.

9. A method as recited in claim 7, wherein said steps of ingesting and topically applying said nutrient system formula are performed simultaneously.

10. A method as recited in claim 1, wherein said nutrient system formula further comprises:
   vitamin E.

11. A method as recited in claim 1, wherein said nutrient system base formula further comprises:
   lecithin.

12. A method as recited in claim 1, further comprising the steps of:
   diluting, succussing and combining said nutrient system formula with an unsuccussed material.

13. A method as recited in claim 1, wherein said nutrient system base formula further comprises:
   aloe.

14. A method for improving the health and appearance of the hair, skin and nails of a person or animal, comprising the steps of:
   providing a nutrient system formula, said nutrient system formula including a nutrient system base formula having lipids, vitamin C, vitamin B7 and silica and a phosphorous nutrient system formula including phosphatidyl serine, phosphatidyl ethanolamine, vitamin B5, vitamin B6 and vitamin D;
   ingesting said nutrient system formula by the person or the animal; and
   topically applying said nutrient system formula on the person or the animal.

15. A method as recited in claim 14, further comprising the step of:
   injecting said nutrient system formula into the person or the animal.

\* \* \* \* \*